(12) United States Patent
Cabri et al.

(10) Patent No.: US 10,800,763 B2
(45) Date of Patent: *Oct. 13, 2020

(54) POLYMORPHIC FORMS OF AFATINIB FREE BASE AND AFATINIB DIMALEATE

(71) Applicant: FRESENIUS KABI ONCOLOGY LTD., New Delhi (IN)

(72) Inventors: Walter Cabri, Milan (IT); Saswata Lahiri, Haryana (IN); Bhuwan Bhaskar Mishra, Haryana (IN); Abul Azim, Haryana (IN); Nilendu Panda, Haryana (IN); Poli Reddy Bhavanam, Haryana (IN); Krishanu Ray, Haryana (IN); Nikunj Kachhadia, Haryana (IN); Kumber Singh, Haryana (IN)

(73) Assignee: Fresenius Kabi Oncology Ltd., New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/735,855

(22) PCT Filed: Jun. 10, 2016

(86) PCT No.: PCT/IB2016/053420
§ 371 (c)(1),
(2) Date: Dec. 12, 2017

(87) PCT Pub. No.: WO2016/199076
PCT Pub. Date: Dec. 15, 2016

(65) Prior Publication Data
US 2018/0312494 A1  Nov. 1, 2018

(30) Foreign Application Priority Data
Jun. 12, 2015 (IN) .......................... 1769/DEL/2015

(51) Int. Cl.
*C07D 405/12* (2006.01)
*C07D 407/12* (2006.01)
*C07C 57/145* (2006.01)

(52) U.S. Cl.
CPC .......... *C07D 405/12* (2013.01); *C07C 57/145* (2013.01); *C07D 407/12* (2013.01); *C07B 2200/13* (2013.01)

(58) Field of Classification Search
CPC .................................................. C07D 405/12
See application file for complete search history.

(56) References Cited

U.S. PATENT DOCUMENTS

| RE43,431 E | 5/2012 | Himmelsbach et al. |
|---|---|---|
| 8,426,586 B2 | 4/2013 | Soyka et al. |
| 8,545,884 B2 | 10/2013 | Messerschmid et al. |
| 10,329,281 B2 * | 6/2019 | Parthasaradhi Reddy ................ C07D 405/12 |
| 10,525,059 B2 * | 1/2020 | Khanna ................ A61K 9/2095 |
| 10,550,107 B2 * | 2/2020 | Srinivasan ............. B01D 9/005 |
| 2005/0085495 A1 | 4/2005 | Soyka et al. |
| 2009/0318480 A1 | 12/2009 | Solca |
| 2014/0051713 A1 | 2/2014 | Gidwani et al. |
| 2017/0240533 A1 * | 8/2017 | Singh ................... A61K 31/517 |

FOREIGN PATENT DOCUMENTS

| CN | 104 744 445 A | 7/2015 |
|---|---|---|
| EP | 3 023 421 A1 | 5/2016 |
| IN | 1769/DEL/2015 A | 12/2016 |
| WO | WO 2012/121764 A1 | 9/2012 |
| WO | WO 2013/052157 A1 | 4/2013 |
| WO | WO 2016/027243 A1 | 2/2016 |
| WO | WO 2016/051380 A1 | 4/2016 |

OTHER PUBLICATIONS

Foreign priority Application No. 1979/CHE/2015 filed Apr. 17, 2015 for WO 2016/166270.*
Caira, "Crystalline Polymorphism of Organic Compounds," *Topics in Current Chemistry*, vol. 198, pp. 163-208, Springer, Berlin, Germany (1998).
Wu et al., "Insensitivity of Compaction Properties of Brittle Granules to Size Enlargement by Roller Compaction," *J. Pharma Sci* 96(5): 1445-1450 (2007).
European Patent Office, International Search Report in International Application No. PCT/IB2016/053420 (dated Feb. 2, 2017).
European Patent Office, Written Opinion in International Application No. PCT/IB2016/053420 (dated Feb. 2, 2017).
International Bureau of WIPO, International Preliminary Report on Patentability in International Application No. PCT/IB2016/053420 (dated Dec. 12, 2017).
European Patent Office, Communication Pursuant to Rule 164(2)(b) and Article 94(3) EPC (dated Apr. 23, 2019).
Balbach et al., "Pharmaceutical evaluation of early development candidates: 'The 100 mg approach'," *International Journal of Pharmaceutics* 275: 1-12 (2004).
*Polymorphism in Pharmaceutical Solids*, H.G. Brittain, editor, Marcel Dekker Inc, New York, 1999, Chapter 1.
Singhal et al., "Drug Polymorphism and Dosage Form Design: A practical perspective," *Advanced Drug Delivery Reviews* 56: 335-347 (2004).
Australian Patent Office, Examination Report No. 1 in Australian Patent Application No. 2016276426 (dated Jan. 11, 2019).

* cited by examiner

*Primary Examiner* — Emily A Bernhardt
(74) *Attorney, Agent, or Firm* — Leydig, Voit & Mayer, Ltd.

(57) ABSTRACT

The present invention relates to crystalline forms of Afatinib and its dimaleate salt. The present invention also relates to processes for the preparation of crystalline forms of Afatinib and its dimaleate salt. The present invention further relates to pharmaceutical compositions of such crystalline forms of Afatinib dimaleate and use thereof in the treatment of a patient in need thereof.

21 Claims, 22 Drawing Sheets

POLYMORPHIC FORMS OF AFATINIB FREE BASE AND AFATINIB DIMALEATE

CROSS REFERENCE TO RELATED PATENT APPLICATION(S)

This patent application is the U.S. national phase of International Application No. PCT/IB2016/053420, filed on Jun. 10, 2016, which claims the benefits of Indian Patent Application No. 1769/DEL/2015, filed 12 Jun. 2015, the disclosures of which are incorporated by reference herein in their entireties for all purposes.

FIELD OF THE INVENTION

The present invention relates to crystalline forms of Afatinib free base and its dimaleate salt. The present invention also relates to processes for the preparation of crystalline forms of Afatinib free base and its dimaleate salt. The present invention further relates to pharmaceutical compositions of such crystalline forms of Afatinib dimaleate and use thereof in the treatment of a patient in need thereof. The present invention further relates to processes for the preparation of crystalline form C of Afatinib dimaleate.

BACKGROUND OF THE INVENTION

Afatinib, chemically known as 4-[(3-chloro-4-fluorophenyl)amino]-6-{[4-(N,N-dimethylamino)-1-oxo-2-buten-1-yl]amino}-7-((S))-tetrahydrofuran-3-yloxy)-quinazoline, is represented by Formula (I).

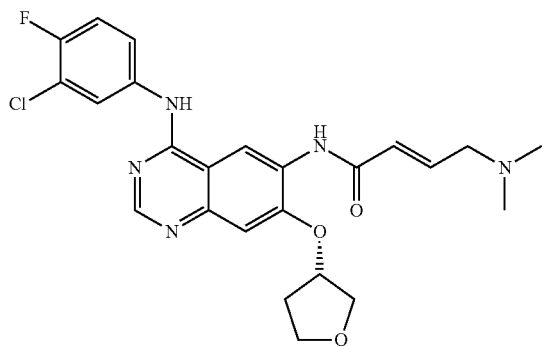

(I)

Afatinib is approved as its dimaleate salt, which is the active ingredient of the drug Gilotrif®. It is an orally administered irreversible inhibitor of both the epidermal growth factor receptor (EGFR) and human epidermal receptor 2 (HER 2) tyrosine kinase and approved for the first-line treatment of patients with metastatic non-small cell lung cancer (NSCLC) whose tumors show exon 19 deletions or exon 21 (L858R) substitution mutations in the epidermal growth factor receptor (EGFR) gene as detected by an FDA-approved test.

The substance Afatinib is disclosed in U.S. RE43,431.

A process for the preparation of Afatinib dimaleate is described in U.S. Pat. No. 8,426,586. The process yields a crystalline polymorph, herein further referred to as "form A". In U.S. Pat. No. 8,426,586 form A of Afatinib dimaleate is characterized by powder X-ray diffraction (XRPD) and differential scanning calorimetry (DSC).

According to U.S. Pat. No. 8,426,586 Afatinib dimaleate only exists in one crystalline modification i.e. form A. However, other crystalline polymorphs of Afatinib dimaleate are also known in the art.

Afatinib dimaleate crystalline forms C, D and E are described in WO 2013/052157. WO2012/121764 describes form B of Afatinib dimaleate, as well as form A, form B and form C of Afatinib free base.

It has been observed in WO 2013/052157, that form A of Afatinib dimaleate as disclosed in U.S. Pat. No. 8,426,586 is hygroscopic in nature and converts to form E of Afatinib dimaleate as described in WO 2013/052157 after absorbing moisture. Form C and form D as disclosed in WO 2013/052157 are not reproducible.

Thus, there is still a need for new polymorphic forms of Afatinib possessing desirable processing properties, such as ease of handling, ease of processing, ease of purification storage stability. Also, there is still a need for intermediate crystal forms that facilitate conversion to other polymorphic forms. New polymorphic forms and solvates of a pharmaceutically useful compound or salt thereof can also provide an opportunity to improve the performance characteristics of an API. It may give advantage to the formulation scientist, by providing a product with different properties, e.g., better processing or handling characteristics, improved dissolution profile, or improved shelf-life.

It has now surprisingly been found that under certain conditions new crystal forms of Afatinib dimaleate and Afatinib free base can be prepared, which are described herein as form F, form G, form H, form I, form J, form K, form L and form M of Afatinib dimaleate and form E and form F of Afatinib free base.

The present invention relates to new crystalline forms of Afatinib dimaleate that have advantageous properties. Such advantageous properties may for example be high chemical purity, e.g. a low content in residual solvents, long lasting storage stability, good flowability, improved solubility and or dissolution rate. Similarly desirable is an advantageous morphology crystal habit, stability against thermal and mechanical stress, resistance to polymorphic conversion, stability to dehydration, a low degree of hygroscopicity. Also, the processing and handling characteristics should be advantageous, e.g. the crystalline forms should be readily grindable, compressible, and they should not electrostatically charge.

SUMMARY OF THE INVENTION

The present invention relates to crystalline polymorphs of Afatinib dimaleate, Afatinib free base and processes for preparing them. The present invention further relates to pharmaceutical compositions comprising such crystalline forms of Afatinib dimaleate and to the use thereof in the treatment of a patient in need thereof. The present invention also relates to processes for the preparation of crystalline form C of Afatinib dimaleate.

In a first aspect, the present invention relates to crystalline form F of Afatinib dimaleate.

In a second aspect, the present invention relates to a process for the preparation of crystalline form F of Afatinib dimaleate, comprising:
 a) dissolving Afatinib in ethyl acetate;
 b) adding maleic acid; and
 c) isolating crystalline form F of Afatinib dimaleate.

In a third aspect, the present invention relates to crystalline form G of Afatinib dimaleate.

In a fourth aspect, the present invention relates to a process for the preparation of crystalline form G of Afatinib dimaleate, comprising:

a) dissolving Afatinib in dimethyl formamide;
b) adding maleic acid;
c) adding methyl tertiary butyl ether; and
d) isolating crystalline form G of Afatinib dimaleate In a fifth aspect, the present invention relates to crystalline form H of Afatinib dimaleate.

In a sixth aspect, the present invention relates to a process for the preparation of crystalline form H of Afatinib dimaleate, comprising:
a) dissolving Afatinib in acetonitrile;
b) adding maleic acid; and
c) isolating crystalline form H of Afatinib dimaleate.

In a seventh aspect, the present invention relates to crystalline form I of Afatinib dimaleate.

In an eighth aspect, the present invention relates to a process for the preparation of crystalline form I of Afatinib dimaleate, comprising:
a) dissolving Afatinib in dimethyl formamide;
b) adding maleic acid;
c) adding dichloromethane; and
d) isolating crystalline form I of Afatinib dimaleate.

In a ninth aspect, the present invention relates to crystalline form J of Afatinib dimaleate.

In a tenth aspect, the present invention relates to a process for the preparation of crystalline form J of Afatinib dimaleate, comprising:
a) dissolving Afatinib in acetone;
b) adding methyl tertiary butyl ether;
c) adding maleic acid: and
d) isolating crystalline form J of Afatinib dimaleate.

In an eleventh aspect, the present invention relates to crystalline form K of Afatinib dimaleate.

In a twelfth aspect, the present invention relates to a process for the preparation of crystalline form K of Afatinib dimaleate, comprising,
a) dissolving Afatinib in ethyl acetate;
b) adding methyl tertiary butyl ether;
c) adding maleic acid: and
d) isolating crystalline form K of Afatinib dimaleate.

In a thirteenth aspect, the present invention relates to crystalline form L of Afatinib dimaleate.

In a fourteenth aspect, the present invention relates to a process for the preparation of crystalline form L of Afatinib dimaleate, comprising:
a) dissolving Afatinib in acetonitrile;
b) adding maleic acid;
c) isolating form H of Afatinib dimaleate;
d) treating with ethyl acetate; and
e) isolating crystalline form L of Afatinib dimaleate.

In a fifteenth aspect, the present invention relates to a process for preparation of crystalline form L of Afatinib dimaleate comprising:
a) treating the crystalline form H of Afatinib dimaleate with ethyl acetate; and
b) isolating crystalline form L of Afatinib dimaleate.

In a sixteenth aspect, the present invention relates to a process for the preparation of crystalline form L of Afatinib dimaleate comprising:

a) reacting a compound of formula II

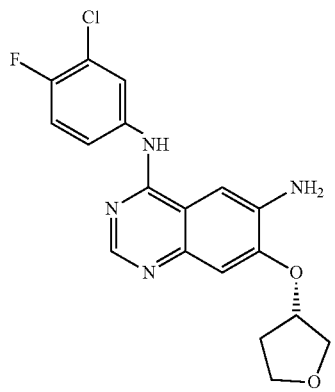

Formula II with a compound of formula III, or a salt thereof

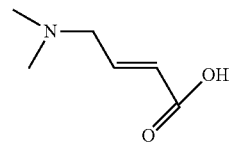

Formula III to obtain Afatinib of formula I,

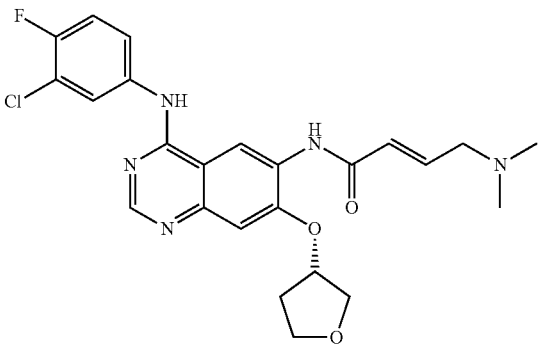

Formula I in the presence of a suitable solvent and dehydrating reagent, at a temperature between −40 to 0° C.; and
b) converting the compound of formula I into the crystalline form L of Afatinib dimaleate.

In a seventeenth aspect, the present invention relates to crystalline form M of Afatinib dimaleate.

In an eighteenth aspect, the present invention relates to a process for the preparation of crystalline form M of Afatinib dimaleate, comprising:
a) dissolving Afatinib in acetonitrile;
b) adding solution of maleic acid in dimethyl sulfoxide and acetonitrile;
c) treating with ethyl acetate; and
d) isolating crystalline form M of Afatinib dimaleate.

In a nineteenth aspect, the present invention relates to crystalline form E of Afatinib free base.

In a twentieth aspect, the present invention relates to a process for the preparation of crystalline form E of Afatinib free base, comprising:

a) dissolving Afatinib in acetone;
b) adding methyl tertiary butyl ether; and
c) isolating crystalline form E of Afatinib free base.

In a twenty-first aspect, the present invention relates to crystalline form F of Afatinib free base.

In a twenty-second aspect, the present invention relates to a process for the preparation of crystalline form F of Afatinib free base, comprising,
a) dissolving Afatinib in dichloromethane;
b) adding methyl tertiary butyl ether; and
c) isolating crystalline form F of Afatinib free base.

In a twenty-third aspect, the present invention relates to a process for the preparation of form C of Afatinib dimaleate, comprising:
a) dissolving Afatinib in acetone;
b) adding maleic acid; and
c) isolating crystalline form C of Afatinib dimaleate.

In a twenty-fourth aspect, the present invention relates to a process for the preparation of form C of Afatinib dimaleate, comprising:
a) treating crystalline form H of Afatinib dimaleate with acetone; and
b) isolating crystalline form C of Afatinib dimaleate.

In a twenty-fifth aspect, the present invention relates to a pharmaceutical composition comprising any one, or a combination of the above described crystalline forms of Afatinib dimaleate, designated as "form F" to "form 11V", and atleast one pharmaceutically acceptable excipient.

In a twenty-sixth aspect, the present invention relates to the use of any one of the above described crystalline forms of Afatinib dimaleate, designated as "form F" to "form M" for the treatment of cancer, particularly for the treatment of solid tumors, including non-small cell lung cancer (NSCLC), breast, head and neck cancer, and a variety of other cancers.

Definitions

As used herein, the expression "ambient temperature" refers to a temperature from about 20° C. to 30° C. Preferably ambient temperature refers to a temperature about 20° C. to about 25° C.

As used herein, the expression "Afatinib" as used herein refers to Afatinib free base prepared according to the method known in art such as described in U.S. RE43,431; U.S. Pat. No. 8,426,586 or as described in Example 1 of the present disclosure.

Abbreviations

| | |
|---|---|
| XRPD | X-ray powder diffraction |
| DSC | Differential scanning calorimetry |
| TGA | Thermal gravimetric analysis |
| 13C-NMR | 13C-Nuclear magnetic resonance |
| IR | Infrared spectroscopy |

DETAILED DESCRIPTION OF THE INVENTION

The crystalline polymorphs according to the present invention may be characterized using various techniques, which are well known to those of ordinary skill in the art.

Examples of characterization methods include, but are not limited to, single crystal X-ray diffraction, X-ray powder diffraction (XRPD, simulated powder X-ray patterns, differential scanning calorimetry (DSC), solid-state 13C-NMR, Raman spectroscopy, infrared spectroscopy (IR), moisture sorption isotherms, thermal gravimetric analysis (TGA), and hot stage techniques.

The crystalline forms F to M of Afatinib dimaleate and forms E and F of Afatinib free base are characterized by X-ray powder diffraction (XRPD), differential scanning calorimetry (DSC) and thermogravimetric analysis (TGA).

Afatinib used as the starting material in the present invention may be prepared according to the method known in art such as described in U.S. RE43,431, U.S. Pat. No. 8,426,586 or as described in Example 1 of the present disclosure.

In a first aspect, the present invention relates to crystalline form F of Afatinib dimaleate.

Figure 1:
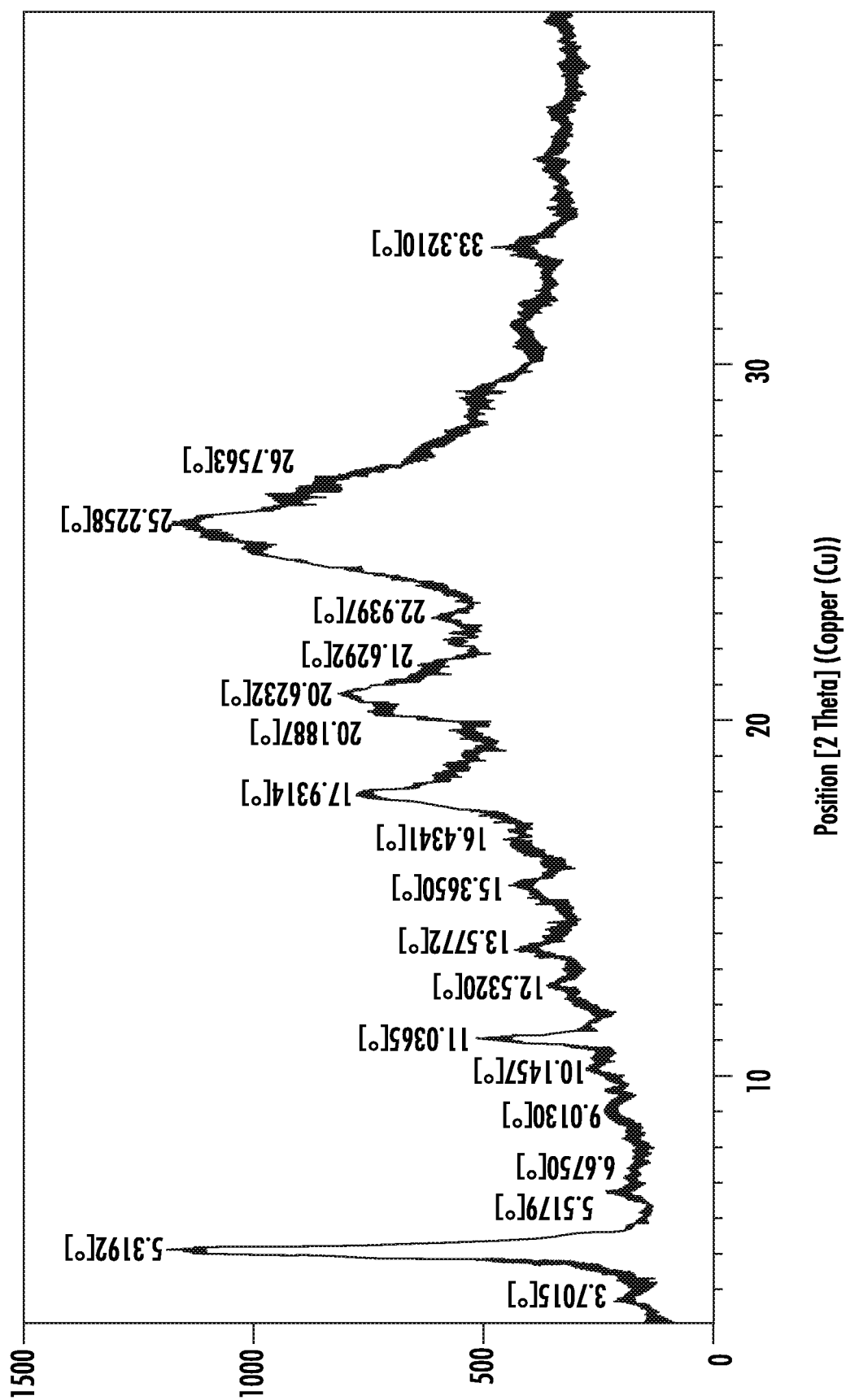
FIG. 1: represents an X-ray powder diffractogram of the crystalline form F of Afatinib dimaleate of the present invention.

Crystalline form F of Afatinib dimaleate is characterized by at least one of:
  a) an X-ray powder diffractogram having peaks at 5.1, 11.0, 17.9, 20.2, 20.8 and 25.7±0.2 degrees two-theta;
  b) an X-ray powder diffractogram substantially the same as depicted in FIG. 1;
  c) an endothermic peak at 115±2° C. as measured by differential scanning calorimetry (DSC); and
  d) a weight loss of about 2.6±1%, as measured by thermogravimetric analysis (TGA).

Crystalline form F of Afatinib dimaleate can be further characterized by an X-ray powder diffractogram having peaks at 3.7, 5.1, 5.5, 6.6, 9.0, 10.1, 11.0, 12.5, 13.6, 15.4, 16.4, 17.9, 20.2, 20.8, 21.6, 22.9, 25.7, 26.8 and 33.3±0.2 degrees two-theta.

Figure 2:
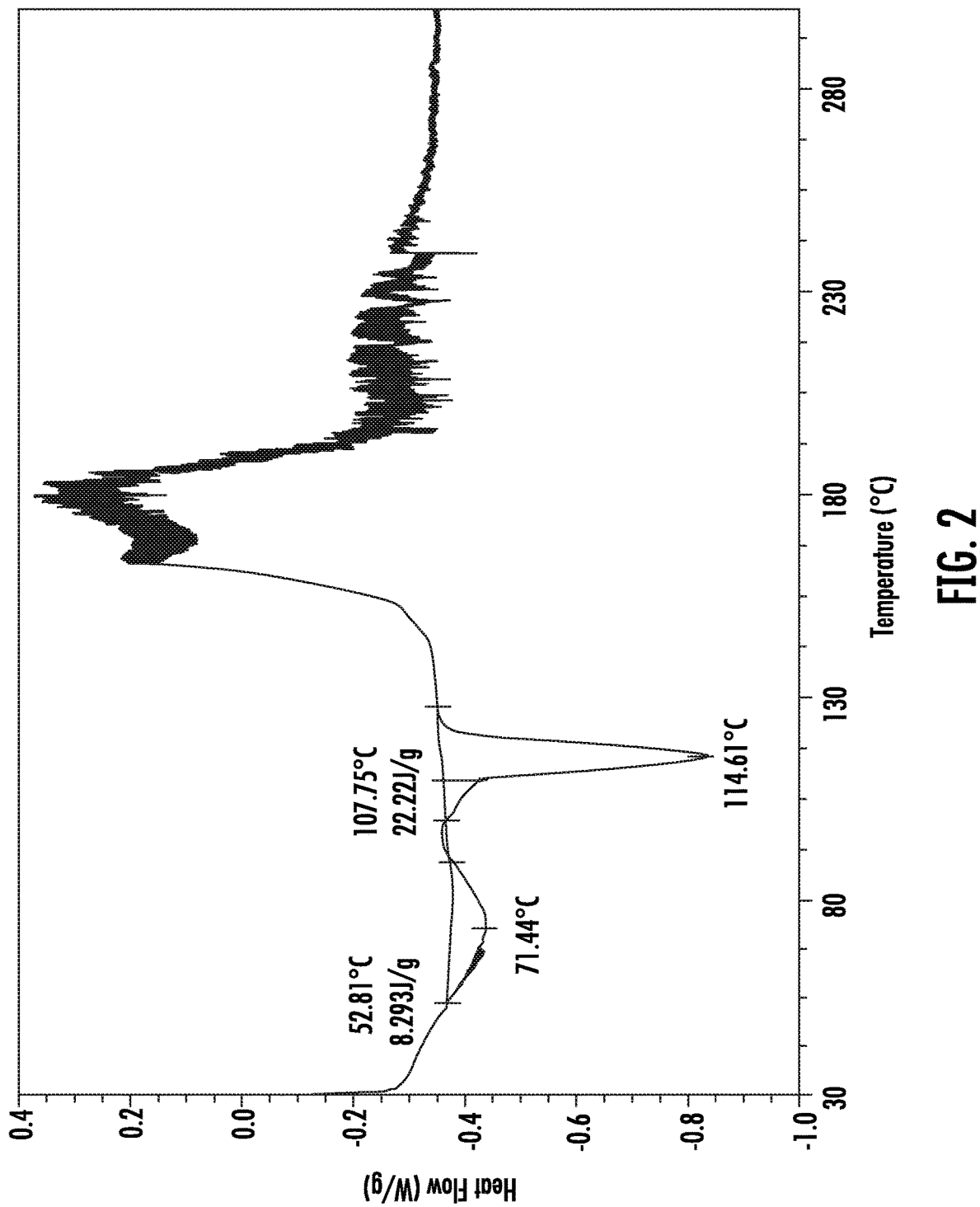
FIG. 2: represents a Differential Scanning calorimetry (DSC) thermogram of the crystalline form F of Afatinib dimaleate of the present invention.

Crystalline form F of Afatinib dimaleate is further characterized by a DSC thermogram substantially the same as depicted in FIG. 2.

In a second aspect, the present invention relates to a process for the preparation of crystalline form F of Afatinib dimaleate, comprising:
  a) dissolving Afatinib in ethyl acetate;
  b) adding maleic acid; and
  c) isolating crystalline form F of Afatinib dimaleate.

Maleic acid in step b may be added as a solution of maleic acid in ethyl acetate.

The solution of Afatinib and maleic acid in ethyl acetate may be obtained at ambient temperature to reflux, preferably at ambient temperature.

Crystalline form F of Afatinib dimaleate may be isolated by any one of the methods selected from extraction, precipitation, cooling, filtration, centrifugation or mixtures thereof. Preferably, crystalline form F of Afatinib dimaleate is isolated by vacuum filtration.

Crystalline form F of Afatinib dimaleate is optionally washed with ethyl acetate to reduce the content of organic volatile impurities. After removal of the solvent the material is dried.

In a third aspect, the present invention relates to crystalline form G of Afatinib dimaleate.

Figure 3:
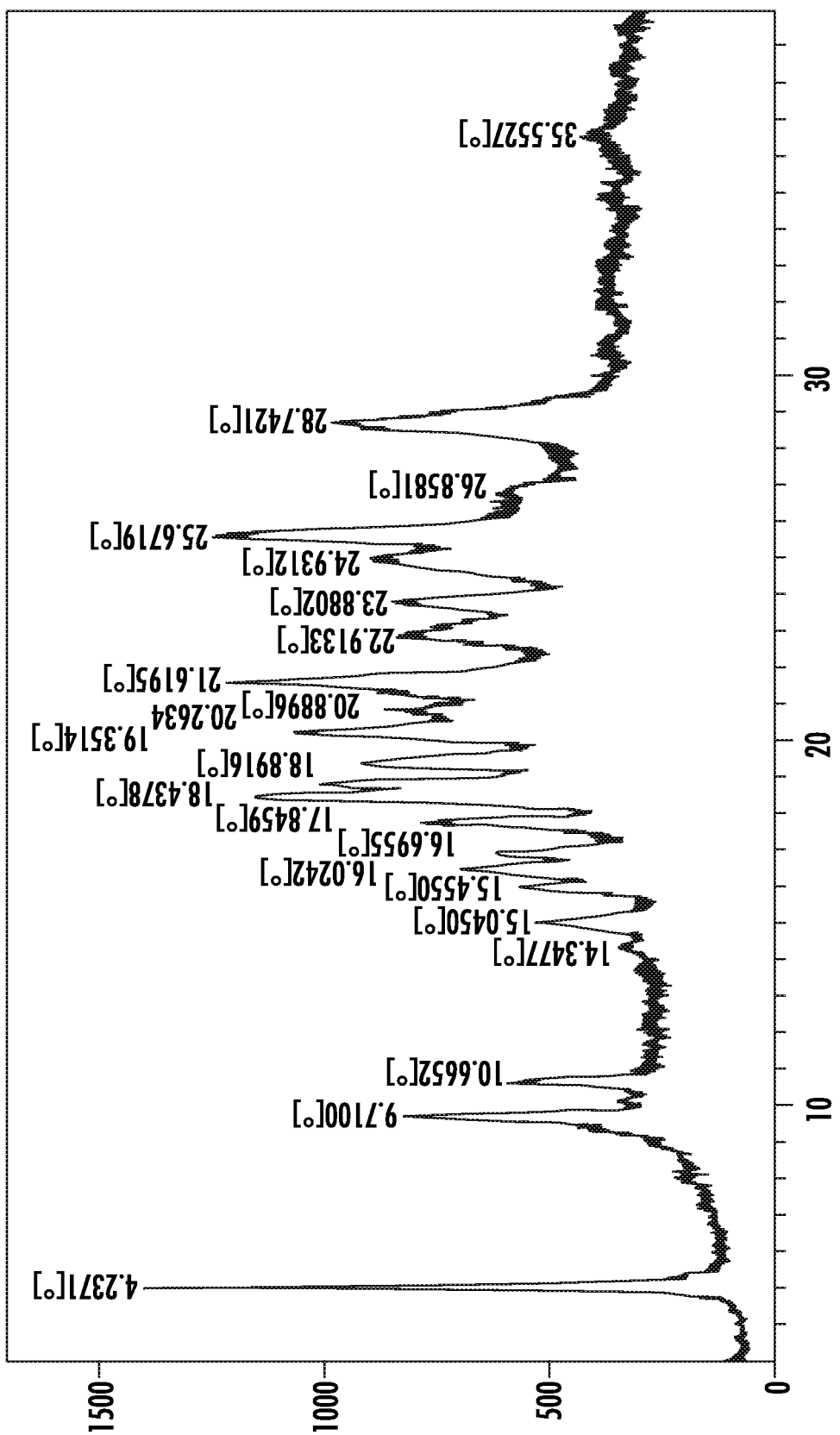
FIG. 3: represents an X-ray powder diffractogram of the crystalline form G of Afatinib dimaleate of the present invention.

Crystalline form G of Afatinib dimaleate is characterized by at least one of:
  a) an X-ray powder diffractogram having peaks at 5.1, 9.7, 10.7, 21.6, 25.7±0.2 degrees two-theta;
  b) an X-ray powder diffractogram substantially the same as depicted in FIG. 3
  c) an endothermic peak at 152±2° C. as measured by differential scanning calorimetry (DSC); and
  d) by a weight loss of about 0.4±1% as measured by thermogravimetric analysis (TGA).

Crystalline form G of Afatinib dimaleate of the present invention can be further characterized by its X-ray powder diffractogram having peaks 5.1, 9.7, 10.7, 14.3, 15.0, 16.0, 16.5, 16.9, 17.8, 17.9, 18.4, 18.8, 19.4, 20.3, 20.9, 21.6, 22.9, 23.9, 24.8, 25.7, 26.9, 28.7 and 36.6±0.2 degrees two-theta.

Figure 4:
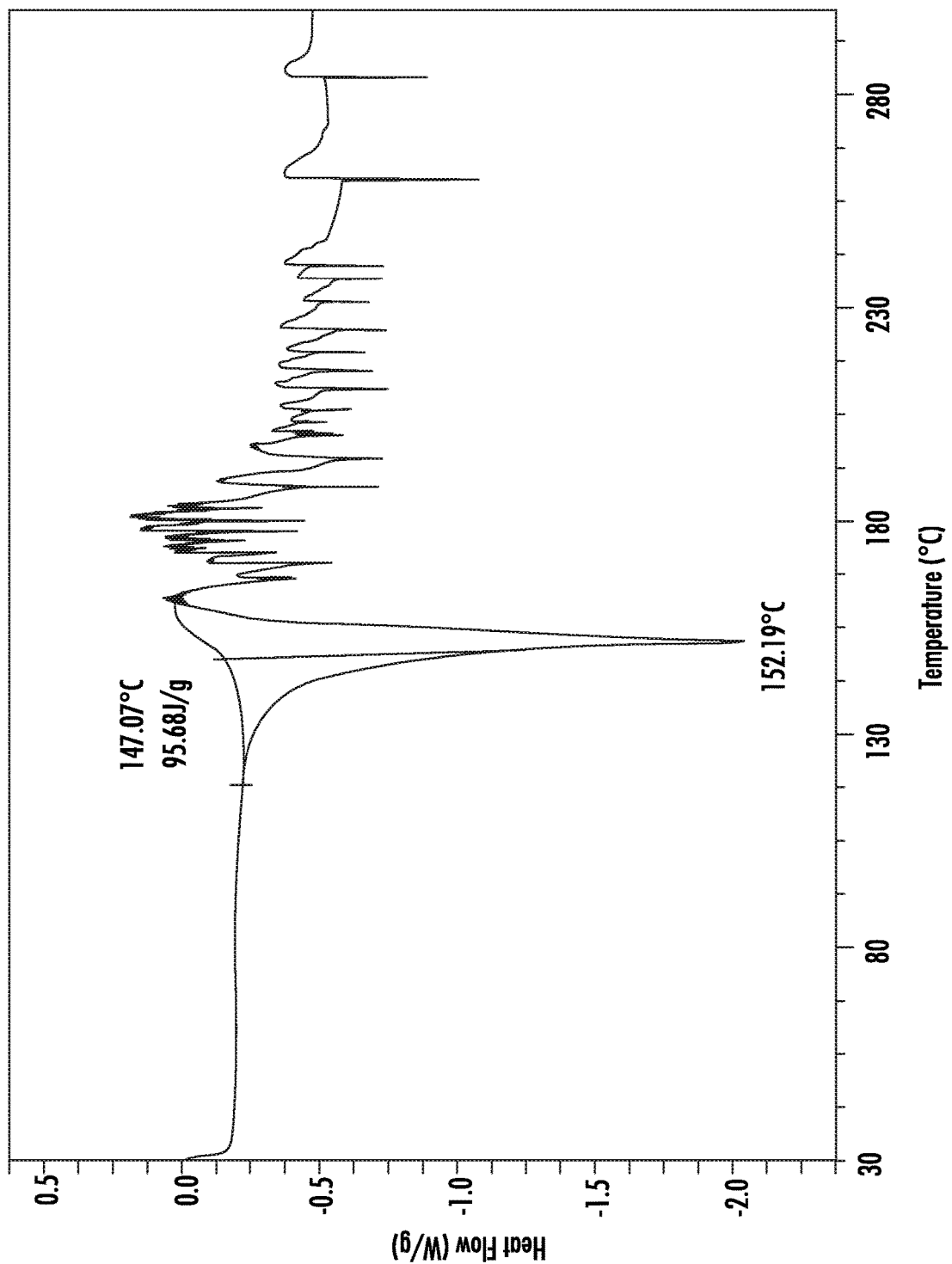
FIG. 4: represents a Differential Scanning calorimetry (DSC) thermogram of the crystalline form G of Afatinib dimaleate of the present invention.

Crystalline form G of Afatinib dimaleate of the present invention is further characterized by its DSC thermogram substantially the same as depicted in FIG. 4.

In a fourth aspect, the present invention relates to a process for the preparation of crystalline form G of Afatinib dimaleate, comprising,
  a) dissolving Afatinib in dimethylformamide;
  b) adding maleic acid;
  c) adding methyl tertiary butyl ether; and
  d) isolating crystalline form G of Afatinib dimaleate.

Maleic acid in step b may be added as a solution of maleic acid in dimethylformamide. It is preferable to cool the reaction mass after step b and prior to step c to a temperature of −5 to 30, preferably 0 to 10° C.

The solution of Afatinib and maleic acid in dimethylformamide may be obtained at ambient temperature to reflux, preferably at ambient temperature.

Crystalline form G of Afatinib dimaleate may be isolated by any one of the methods selected from extraction, precipitation, cooling, filtration, centrifugation or mixture thereof, preferably crystalline form G of Afatinib dimaleate is isolated by using vacuum filtration.

Crystalline form G of Afatinib dimaleate is optionally washed with methyl tertiary butyl ether to reduce the content of organic volatile impurities. After removal of the solvent the material is dried.

In a fifth aspect, the present invention relates to crystalline form H of Afatinib dimaleate.

Figure 5:
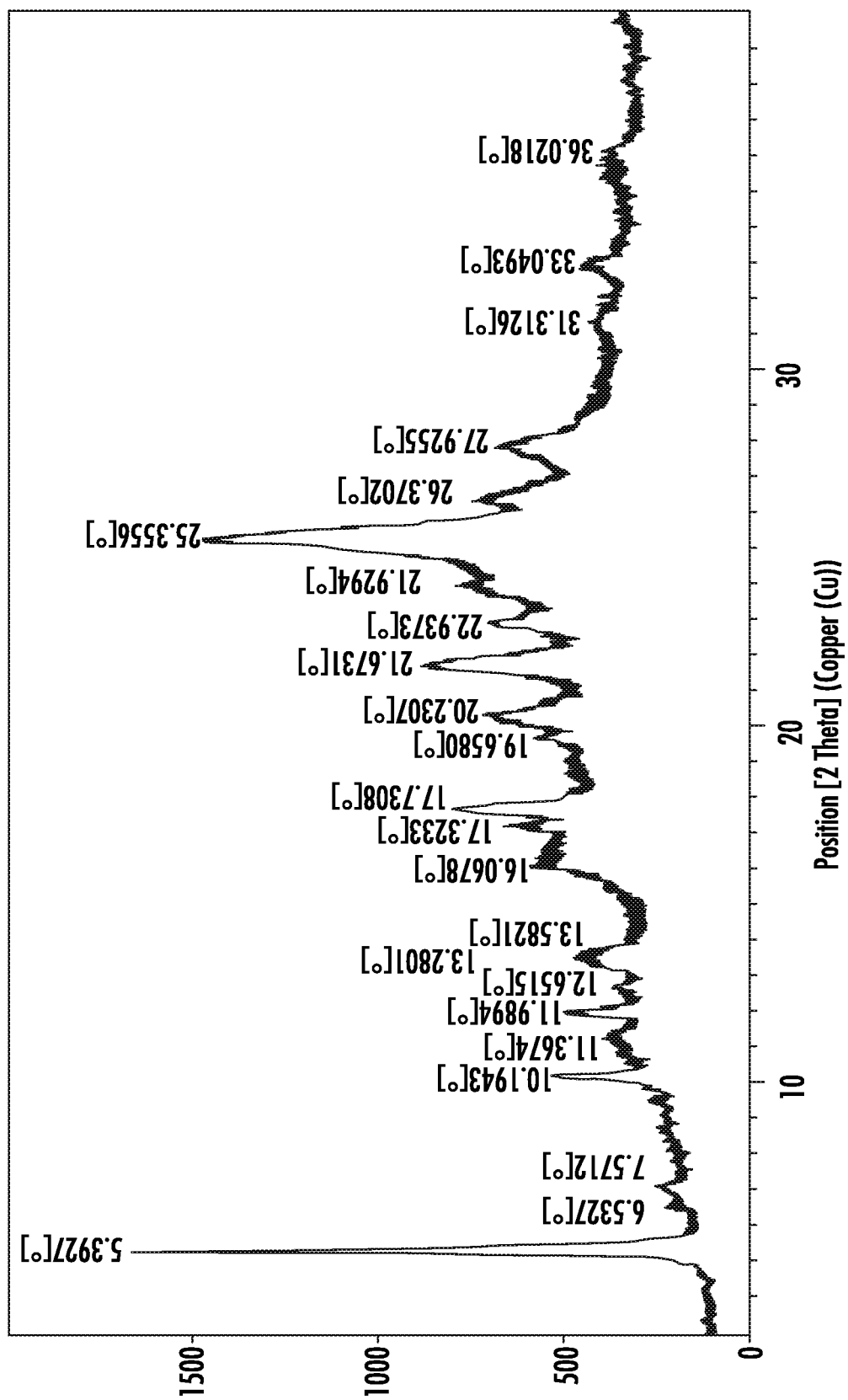
FIG. 5: represents an X-ray powder diffractogram of the crystalline form H of Afatinib dimaleate of the present invention

Crystalline form H of Afatinib dimaleate is characterized by at least one of:
  a) an X-ray powder diffractogram having peaks at 5.4, 6.5, 10.2, 12.7, 17.7, 21.7, and 25.3±0.2 degrees two-theta;
  b) an X-ray powder diffractogram substantially the same as depicted in FIG. 5
  c) an endothermic peak at 118±2° C. as measured by differential scanning calorimetry (DSC); and
  d) by a weight loss of about 0.6±1% as measured by thermogravimetric analysis (TGA).

Crystalline form H of Afatinib dimaleate can be further characterized by its X-ray powder diffractogram having peaks at 5.4, 6.5, 7.1, 10.2, 11.4, 12.0, 12.7, 13.2, 13.6, 16.1, 17.2, 17.7, 19.7, 20.3, 21.7, 22.9, 23.9, 25.3, 26.4, 27.9, 31.3, 33.0 and 36.1±0.2 degrees two-theta.

Figure 6:
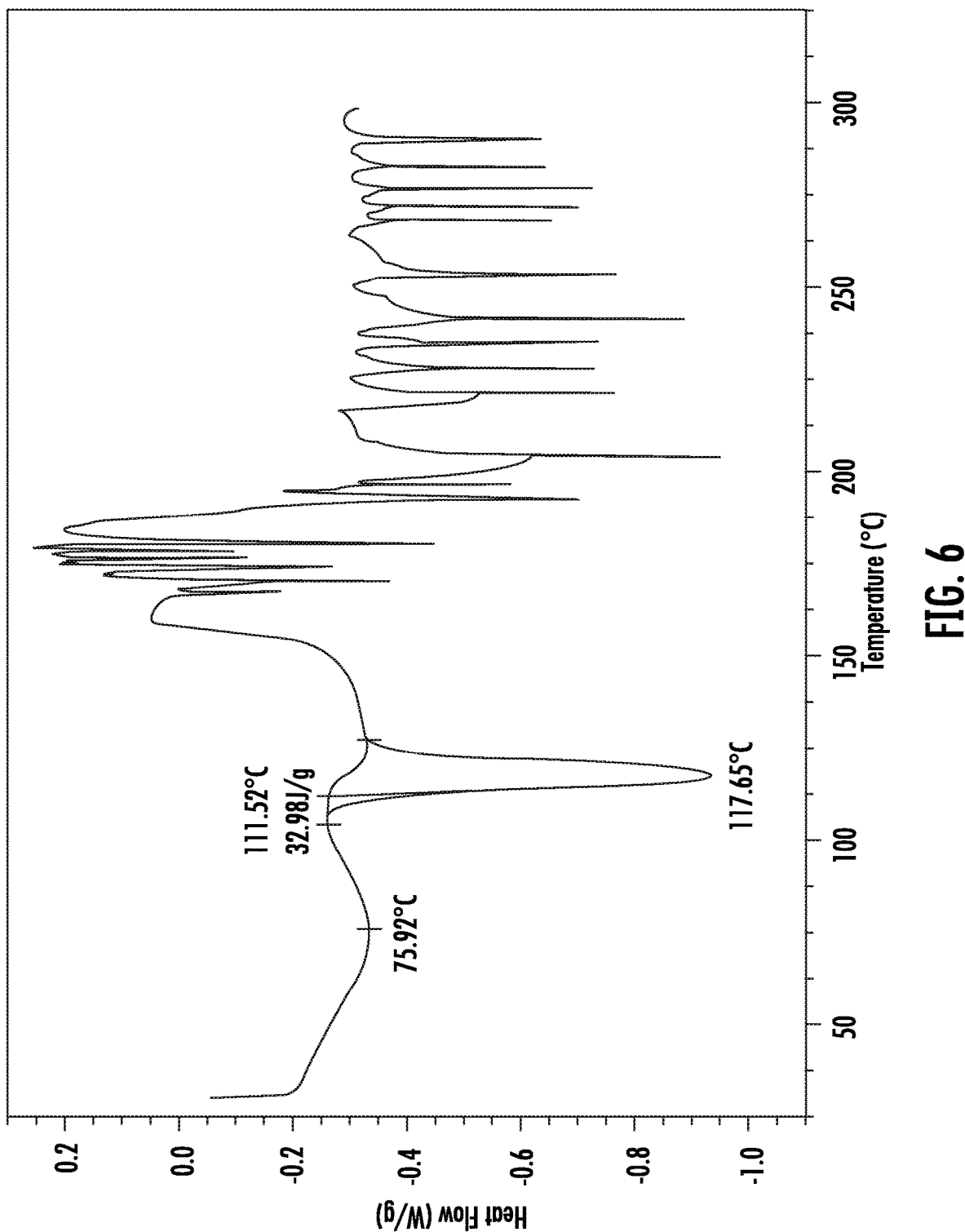
FIG. 6: represents a Differential Scanning calorimetry (DSC) thermogram of the crystalline form H of Afatinib dimaleate of the present invention

Crystalline form H of Afatinib dimaleate further characterized by its DSC thermogram substantially the same as depicted in FIG. 6.

In a sixth aspect, the present invention relates to a process for the preparation of crystalline form H of Afatinib dimaleate, comprising:
  a) dissolving Afatinib in acetonitrile;
  b) adding maleic acid; and
  c) isolating crystalline form H of Afatinib dimaleate.

Maleic acid in step b is added as a solution of maleic acid in acetonitrile.

The solution of Afatinib and maleic acid in acetonitrile may be obtained at ambient temperature or reflux, preferably at ambient temperature.

Crystalline form H of Afatinib dimaleate may be isolated by any one of the methods selected from extraction, precipitation, cooling, filtration, centrifugation or mixture thereof. Preferably crystalline form H of Afatinib dimaleate is isolated by using vacuum filtration.

Crystalline form H of Afatinib dimaleate is optionally washed with acetonitrile to reduce the content of organic volatile impurities. After removal of the solvent the material is dried.

In a seventh aspect, the present invention relates to crystalline form I of Afatinib dimaleate.

Figure 7:
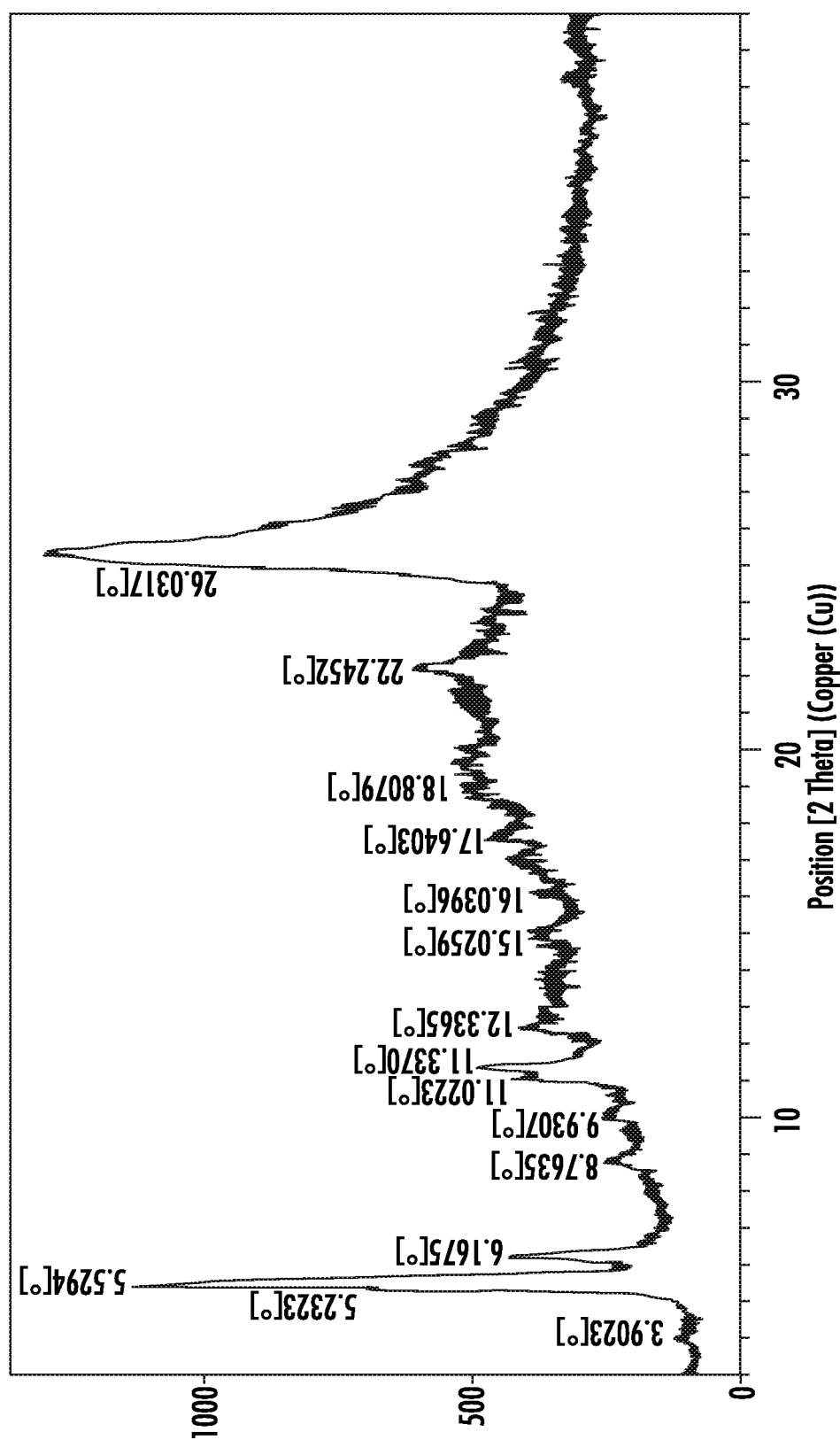
FIG. 7: represents an X-ray powder diffractogram of the crystalline form I of Afatinib dimaleate of the present invention

Crystalline form I of Afatinib dimaleate is characterized by at least one of:
  a) an X-ray powder diffractogram having peaks at 5.5, 6.2, 11.3, 22.2 and 25.1±0.2 degrees two-theta;
  b) an X-ray powder diffractogram substantially the same as depicted in FIG. 7
  c) endothermic peaks at 114 and 169±2° C. as measured by differential scanning calorimetry (DSC); and
  d) a weight loss of about 4.2±1% as measured by thermogravimetric analysis (TGA).

Figure 8:
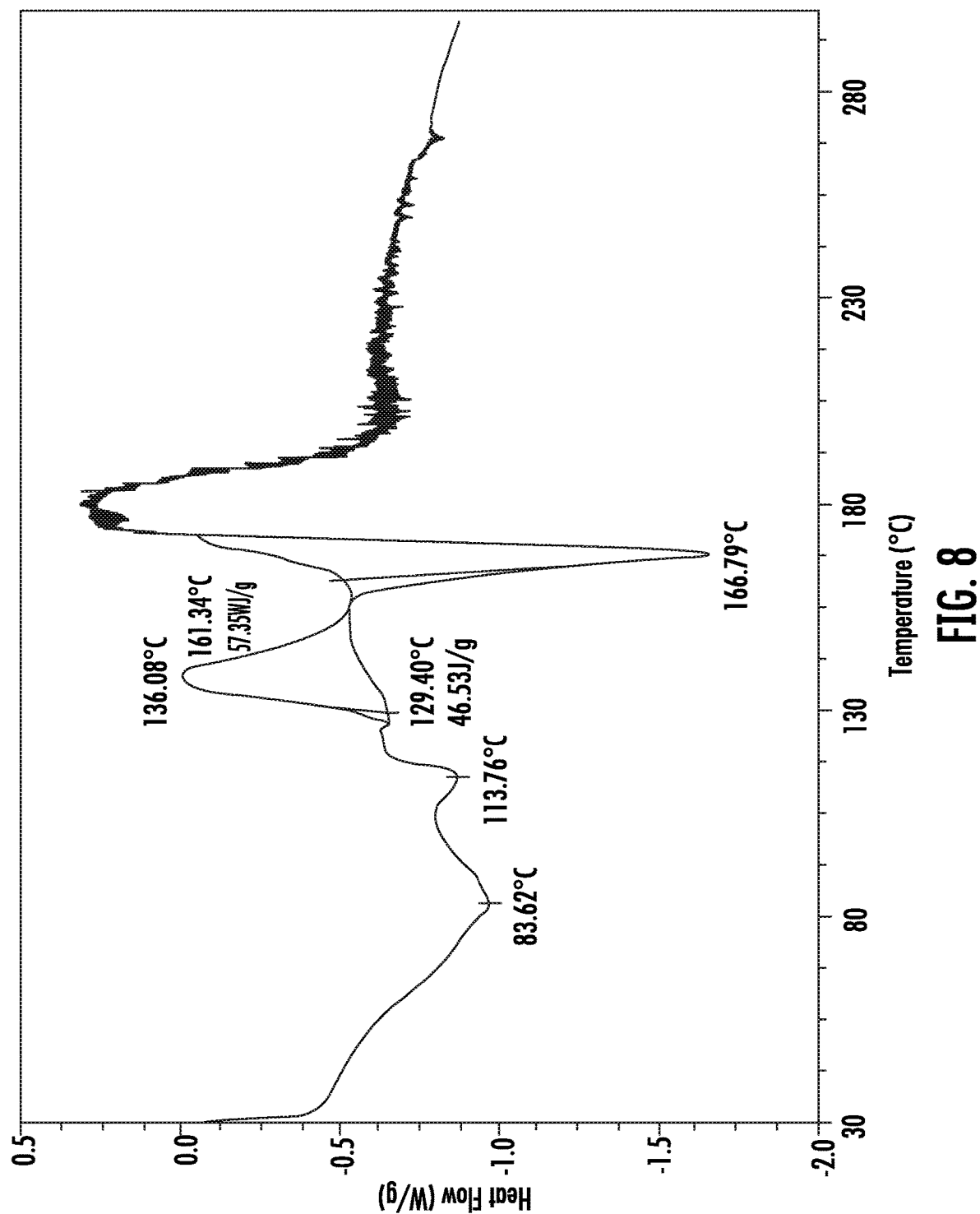
FIG. 8: represents a Differential Scanning calorimetry (DSC) thermogram of the crystalline form I of Afatinib dimaleate of the present invention

Crystalline form I of Afatinib dimaleate can be further characterized by its X-ray powder diffractogram having peaks at 3.9, 5.3, 5.5, 5.6, 6.2, 8.8, 10.0, 11.0, 11.3, 12.4, 15.0, 16.0, 17.6, 18.8, 22.2 and 25.1±0.2 degrees two-theta Crystalline form I of Afatinib dimaleate of the present invention is further characterized by its DSC thermogram substantially the same as depicted in FIG. 8.

In an eighth aspect, the present invention relates to a process for the preparation of crystalline form I of Afatinib dimaleate, comprising:
  a) dissolving Afatinib in dimethyl formamide;
  b) adding maleic acid;
  c) adding dichloromethane; and
  d) isolating crystalline form I of Afatinib dimaleate.

Maleic acid in step b may be added as a solution of maleic acid in dimethyl formamide.

The solution of Afatinib and maleic acid in dimethyl formamide may be obtained at ambient temperature to reflux, preferably at ambient temperature.

Crystalline form I of Afatinib dimaleate may be isolated by any one of the method selected from extraction, precipitation, cooling, filtration, centrifugation or mixture thereof. Preferably, crystalline form I of Afatinib dimaleate is isolated by vacuum filtration.

Crystalline form I of Afatinib dimaleate is optionally washed with dichloromethane to reduce the content of organic volatile impurities. After removal of the solvent the material is dried.

In a ninth aspect, the present invention relates to crystalline form J of Afatinib dimaleate.

Figure 9:
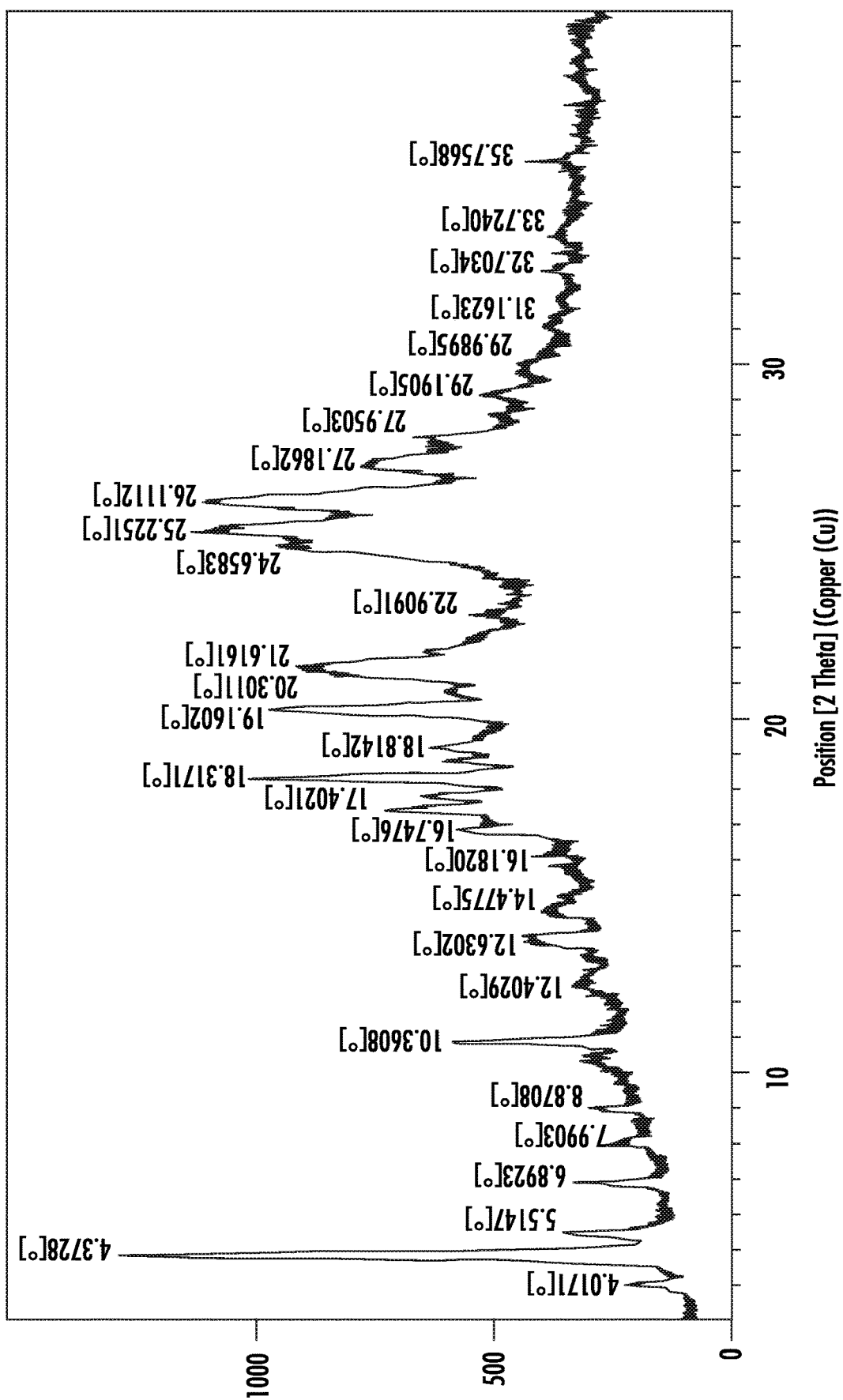
FIG. 9: represents an X-ray powder diffractogram of the crystalline form J of Afatinib dimaleate of the present invention

Crystalline form J of Afatinib dimaleate is characterized by at least one of:
  a) an X-ray powder diffractogram having peaks at 4.9, 10.9, 18.3, 20.3, 25.3 and 26.1, ±0.2 degrees two-theta;
  b) an X-ray powder diffractogram substantially the same as depicted in FIG. 9
  c) endothermic peaks at 123, 136 and 158±2° C. as measured by differential scanning calorimetry (DSC); and
  d) by a weight loss of about 1.9±1% as measured by thermogravimetric analysis (TGA).

Crystalline form J of Afatinib dimaleate can be further characterized by its X-ray powder diffractogram having peaks at 4.0, 4.9, 5.5, 6.9, 8.0, 9.0, 10.9, 12.4, 13.6, 13.9, 14.5, 16.2, 16.7, 17.4, 17.8, 18.3, 18.8, 19.2, 20.3, 21.3, 21.6, 23.0, 24.8, 25.3, 26.1, 27.2, 28, 29.2, 29.9, 31.2, 32.7, 33.7 and 35.8±0.2 degrees two-theta.

Figure 10:
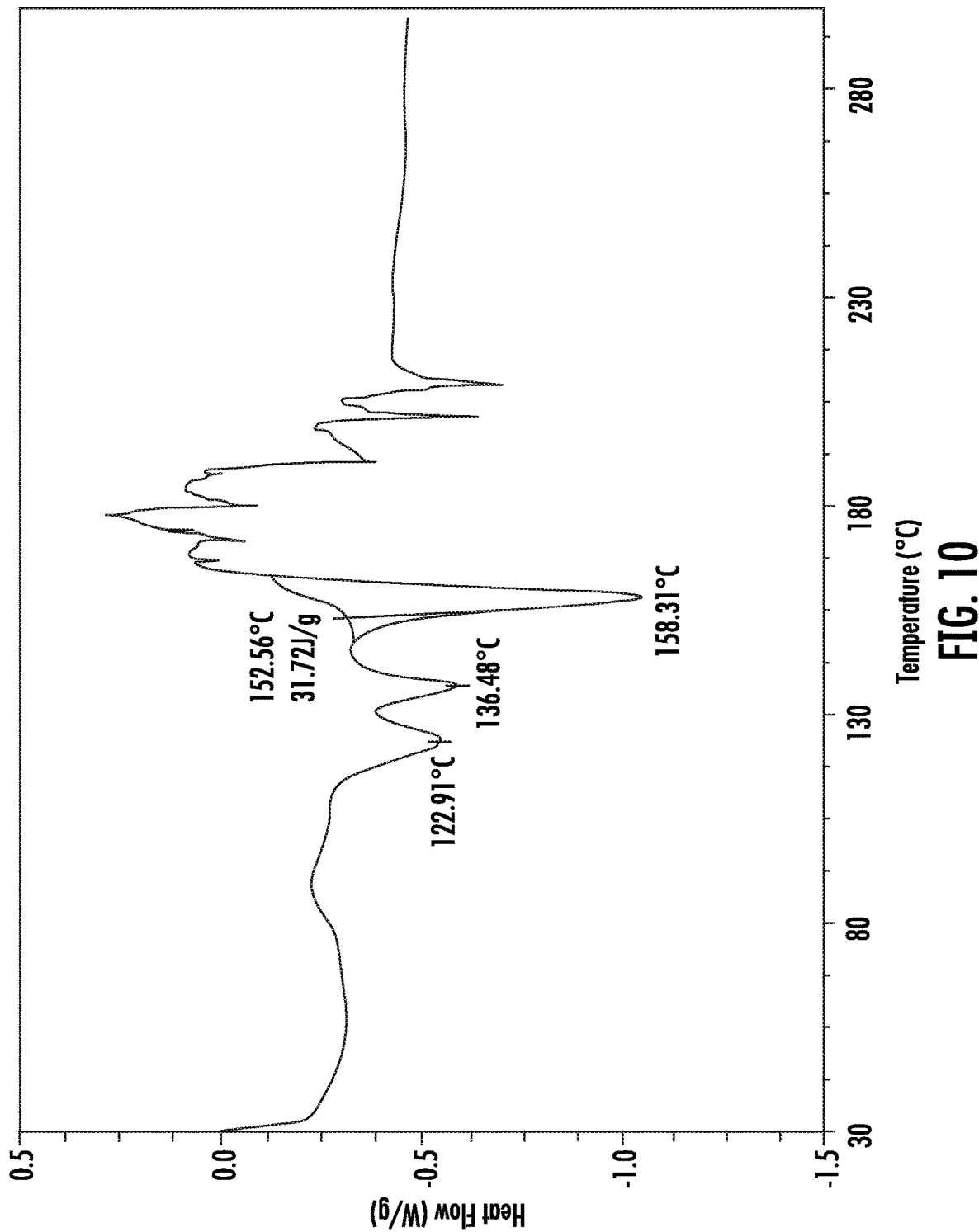
FIG. 10: represents a Differential Scanning calorimetry (DSC) thermogram of the crystalline form J of Afatinib dimaleate of the present invention

Crystalline form J of Afatinib dimaleate of the present invention is further characterized by its DSC thermogram substantially the same as depicted in FIG. 10.

In a tenth aspect, the present invention relates to a process for the preparation of crystalline form J of Afatinib dimaleate, comprising:
  a) dissolving Afatinib in acetone;
  b) adding methyl tertiary butyl ether;
  c) adding maleic acid; and
  d) isolating crystalline form J of Afatinib dimaleate.

Maleic acid in step c may be added as a solution of maleic acid in acetone.

The solution of Afatinib and maleic acid in acetone may be obtained at ambient temperature to reflux, preferably at ambient temperature.

Crystalline form J of Afatinib dimaleate may be isolated by any one of the method selected from extraction, precipitation, cooling, filtration, centrifugation or mixture thereof. Preferably form J of Afatinib dimaleate is isolated by vacuum filtration. Crystalline form J of Afatinib dimaleate is optionally washed with methyl tertiarybutyl ether to reduce the organic volatile impurities content. After removal of the solvent the material is dried.

In an eleventh aspect, the present invention relates to crystalline form K of Afatinib dimaleate.

Figure 11:
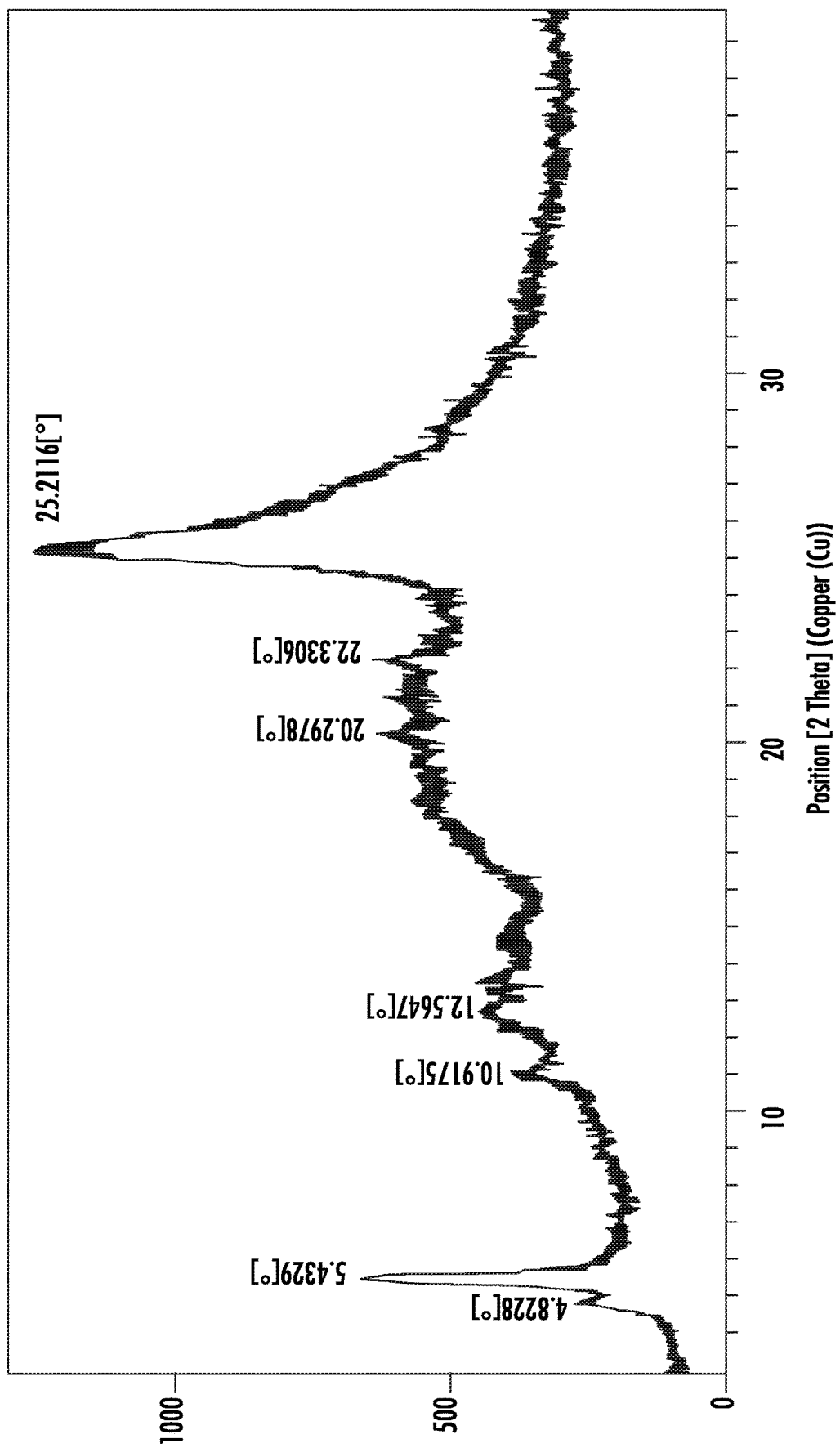
FIG. 11: represents an X-ray powder diffractogram of the crystalline form K of Afatinib dimaleate of the present invention

Crystalline form K of Afatinib dimaleate is characterized by at least one of:
  a) an X-ray powder diffractogram having peaks at 4.9, 5.4, 22.3, and 25.2±0.2 degrees two-theta;
  b) an X-ray powder diffractogram substantially the same as depicted in FIG. 11
  c) endothermic peaks at 105, 129 and 166±2° C. as measured by differential scanning calorimetry (DSC); and
  d) by a weight loss of about 0.8±1% as measured by thermogravimetric analysis (TGA).

Crystalline form K of Afatinib dimaleate can be further characterized by its X-ray powder diffractogram having peaks at 4.9, 5.4, 11.0, 12.7, 20.3, 22.3 and 25.2±0.2 degrees two-theta.

Figure 12:
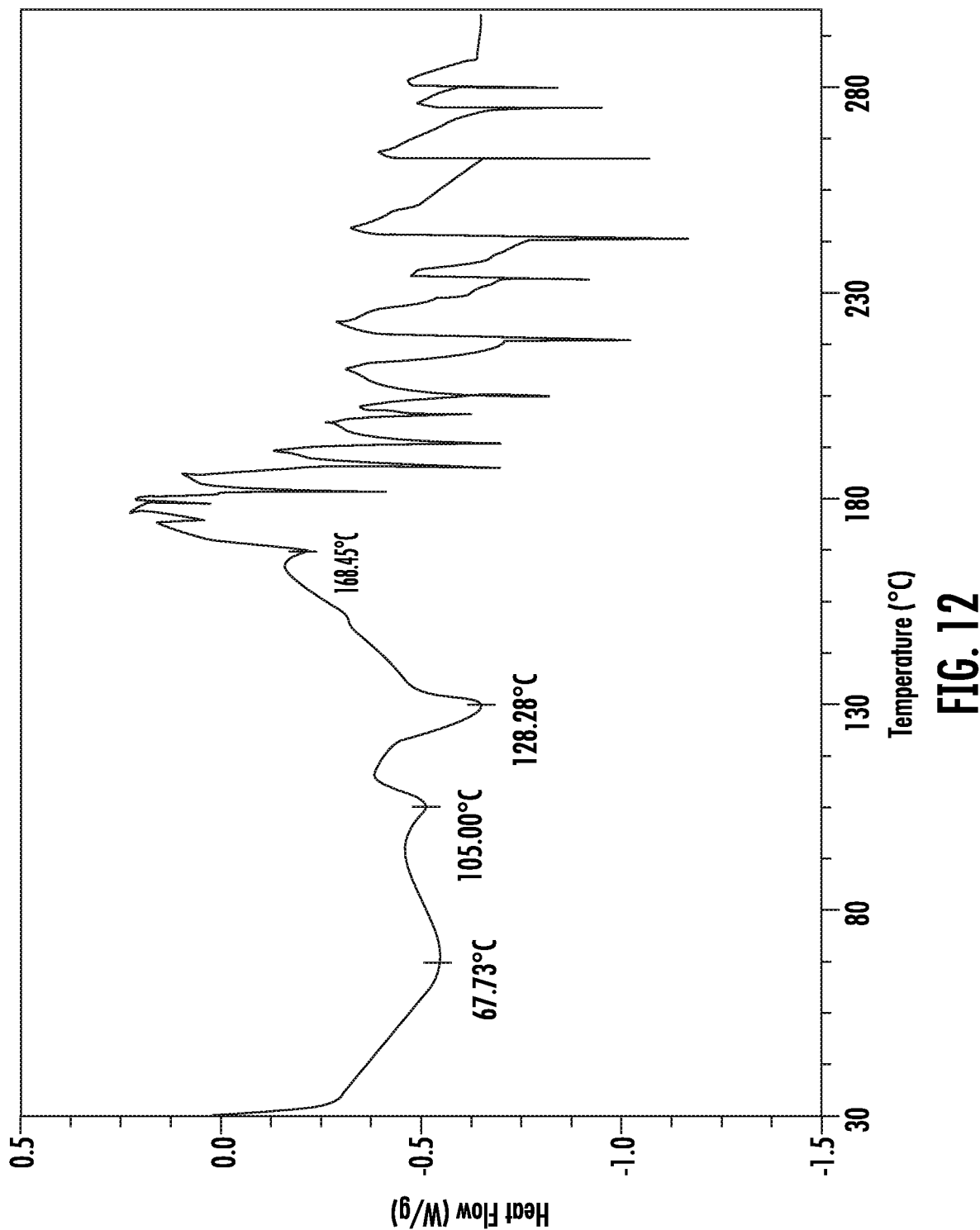
FIG. 12: represents a Differential Scanning calorimetry (DSC) thermogram of the crystalline form K of Afatinib dimaleate of the present invention

Crystalline form K of Afatinib dimaleate of the present invention is further characterized by its DSC thermogram substantially the same as depicted in FIG. 12.

In a twelfth aspect, the present invention relates to a process for the preparation of crystalline form K of Afatinib dimaleate, comprising:
  a) dissolving Afatinib in ethyl acetate;
  b) adding methyl tertiary butyl ether;
  c) adding maleic acid; and
  d) isolating crystalline form K of Afatinib dimaleate.

Maleic acid in step c may be added as a solution of maleic acid in ethyl acetate.

The solution of Afatinib and maleic acid in ethyl acetate may be obtained at ambient temperature to reflux, preferably at ambient temperature.

Crystalline form K of Afatinib dimaleate may be isolated by any one of the method selected from extraction, precipitation, cooling, filtration, centrifugation or mixture thereof. Preferably, crystalline form K of Afatinib dimaleate is isolated by vacuum filtration.

Crystalline form K of Afatinib dimaleate is optionally washed with methyl tertiarybutyl ether to reduce the content of organic volatile impurities. After removal of the solvent the material is dried.

In a thirteenth aspect, the present invention relates to crystalline form L of Afatinib dimaleate.

Figure 13:
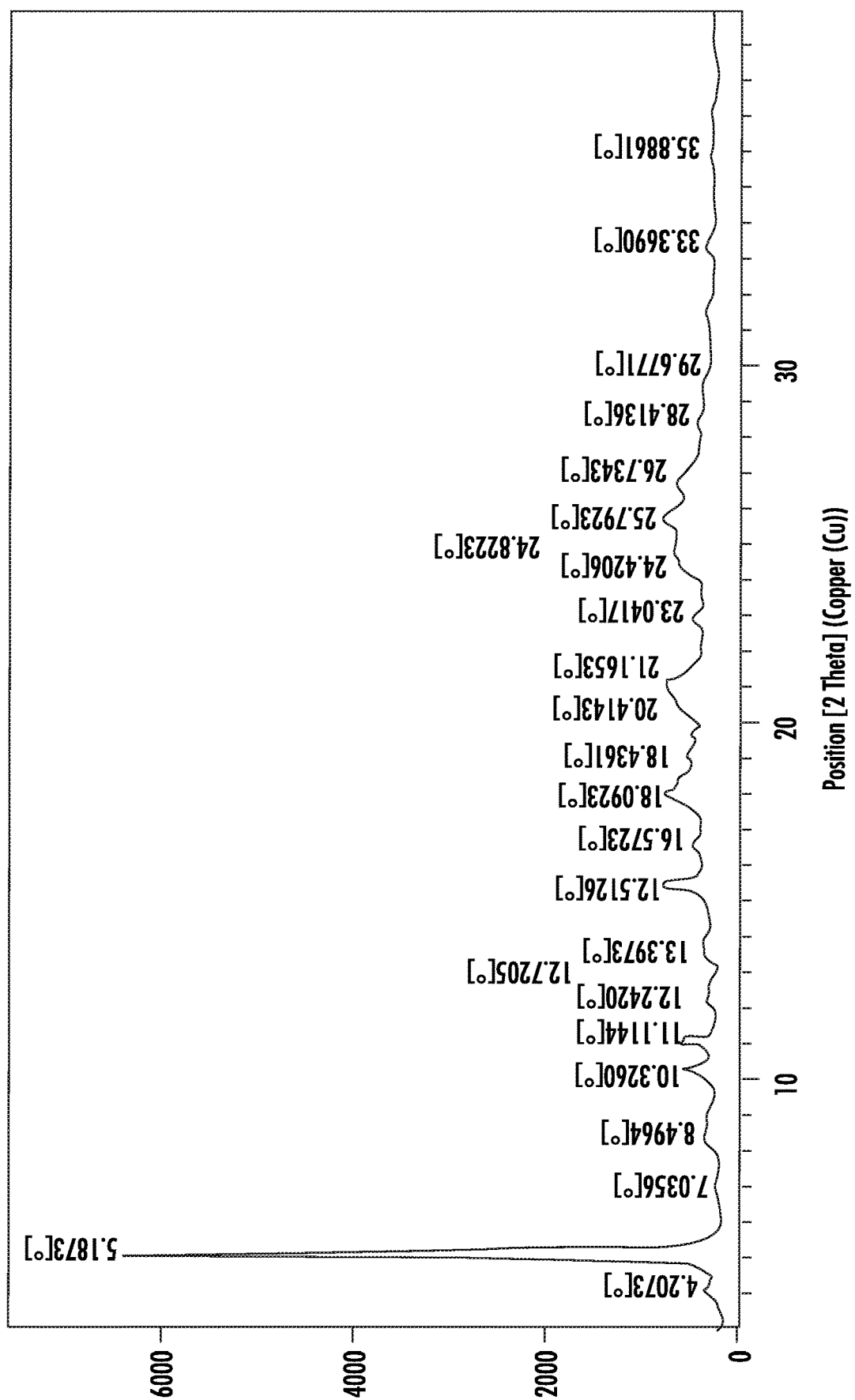
FIG. 13: represents an X-ray powder diffractogram of the crystalline form L of Afatinib dimaleate of the present invention

Crystalline form L of Afatinib dimaleate is characterized by at least one of:

a) an X-ray powder diffractogram having peaks at 5.2, 10.3, 11.1, 15.5, 18.1±0.2 degrees two-theta;

b) an X-ray powder diffractogram substantially the same as depicted in FIG. 13;

c) endothermic peaks at 125 and 171±2° C. as measured by differential scanning calorimetry (DSC); and d) a weight loss of about 2.0±1% as measured by thermogravimetric analysis (TGA).

Crystalline form L of Afatinib dimaleate of the present invention can be further characterized by its X-ray powder diffractogram having peaks at 4.2, 5.2, 7.0, 8.5, 10.3, 11.1, 12.2, 12.7, 13.4, 15.5, 16.6, 18.1, 18.4, 20.4, 21.2, 23.0, 24.4, 24.9, 25.7, 26.7, 28.4, 29.7, 33.4 and 35.9±0.2 degrees two-theta.

Figure 14:
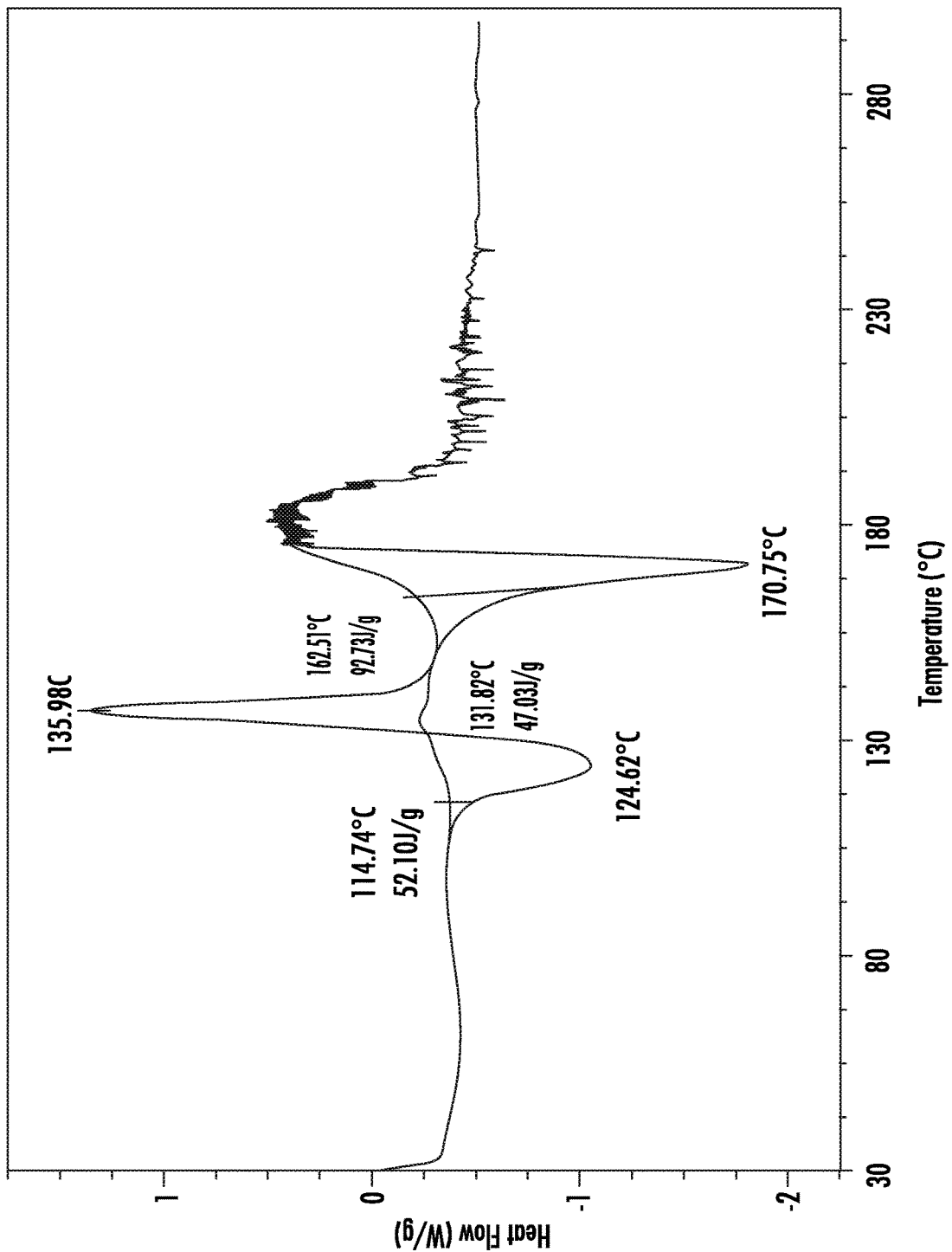
FIG. 14: represents a Differential Scanning calorimetry (DSC) thermogram of the crystalline form L of Afatinib dimaleate of the present invention

Crystalline form L of Afatinib dimaleate of the present invention is further characterized by its DSC thermogram substantially the same as depicted in FIG. 14.

In a fourteenth aspect, the present invention relates to a process for the preparation of crystalline form L of Afatinib dimaleate, comprising:

a) dissolving Afatinib in acetonitrile;

b) adding maleic acid;

c) isolating form H of Afatinib dimaleate;

d) treating with ethyl acetate; and e) isolating crystalline form L of Afatinib dimaleate.

Maleic acid in step b may be added as a solution of maleic acid in acetonitrile.

The solution of Afatinib and maleic acid in acetonitrile may be obtained at ambient temperature to reflux, preferably at ambient temperature.

Crystalline form L of Afatinib dimaleate may be isolated by any one of the method selected from extraction, precipitation, cooling, filtration, centrifugation or mixture thereof. Preferably crystalline form L of Afatinib dimaleate is isolated by vacuum filtration.

Crystalline form L of Afatinib dimaleate is optionally washed with ethyl acetate to reduce the organic volatile impurities content. After removal of the solvent the material is dried.

In a fifteenth aspect, the present invention relates to a process for the preparation of crystalline form L of Afatinib dimaleate, comprising:

a) treating the crystalline form H of Afatinib dimaleate with ethyl acetate; and b) isolating crystalline form L of Afatinib dimaleate.

Crystalline form L of Afatinib dimaleate is optionally washed with ethyl acetate to reduce the content of organic volatile impurities. After removal of the solvent the material was dried.

Crystalline form L of Afatinib dimaleate may be isolated by any one of the method selected from extraction, precipitation, cooling, filtration, centrifugation or mixture thereof. Preferably crystalline form L of Afatinib dimaleate is isolated by using vacuum filtration.

In a sixteenth aspect, the present invention relates to a process for the preparation of crystalline form L of Afatinib dimaleate, comprising:

a) reacting a compound of formula II

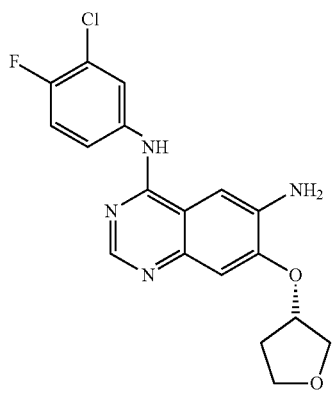

Formula II with a compound of formula III, or a salt thereof

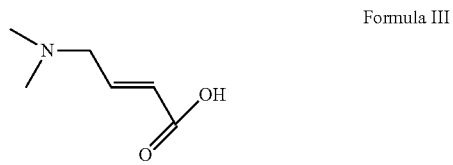

Formula III to obtain Afatinib of formula I,

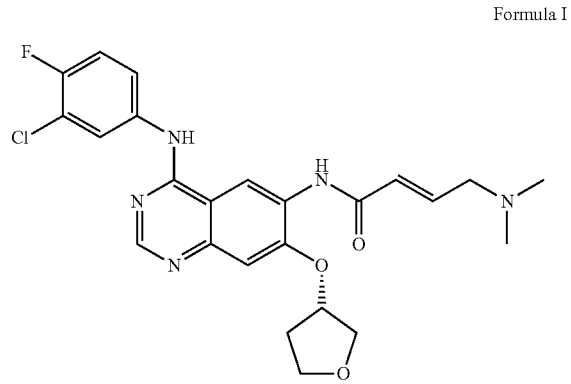

Formula I in the presence of a suitable solvent and dehydrating reagent, at a temperature between −40 to 0° C.; and b) converting the compound of formula I into the crystalline form L of Afatinib dimaleate.

Wherein in step a, reaction of compound II and III may be carried out at the temperature −25 to −10° C.

The dehydrating agent used in the above process is thionyl chloride.

wherein in step a) of the above process, the solvent is selected from hydrocarbons, esters, ketones, halogenated hydrocarbons, ethers, nitriles, alcohols, amides, sulfoxides and mixtures thereof, preferably, the solvent is an amide, more preferably the solvent is dimethylacetamide.

In a seventeenth aspect, the present invention relates to crystalline form M of Afatinib dimaleate.

Figure 15:
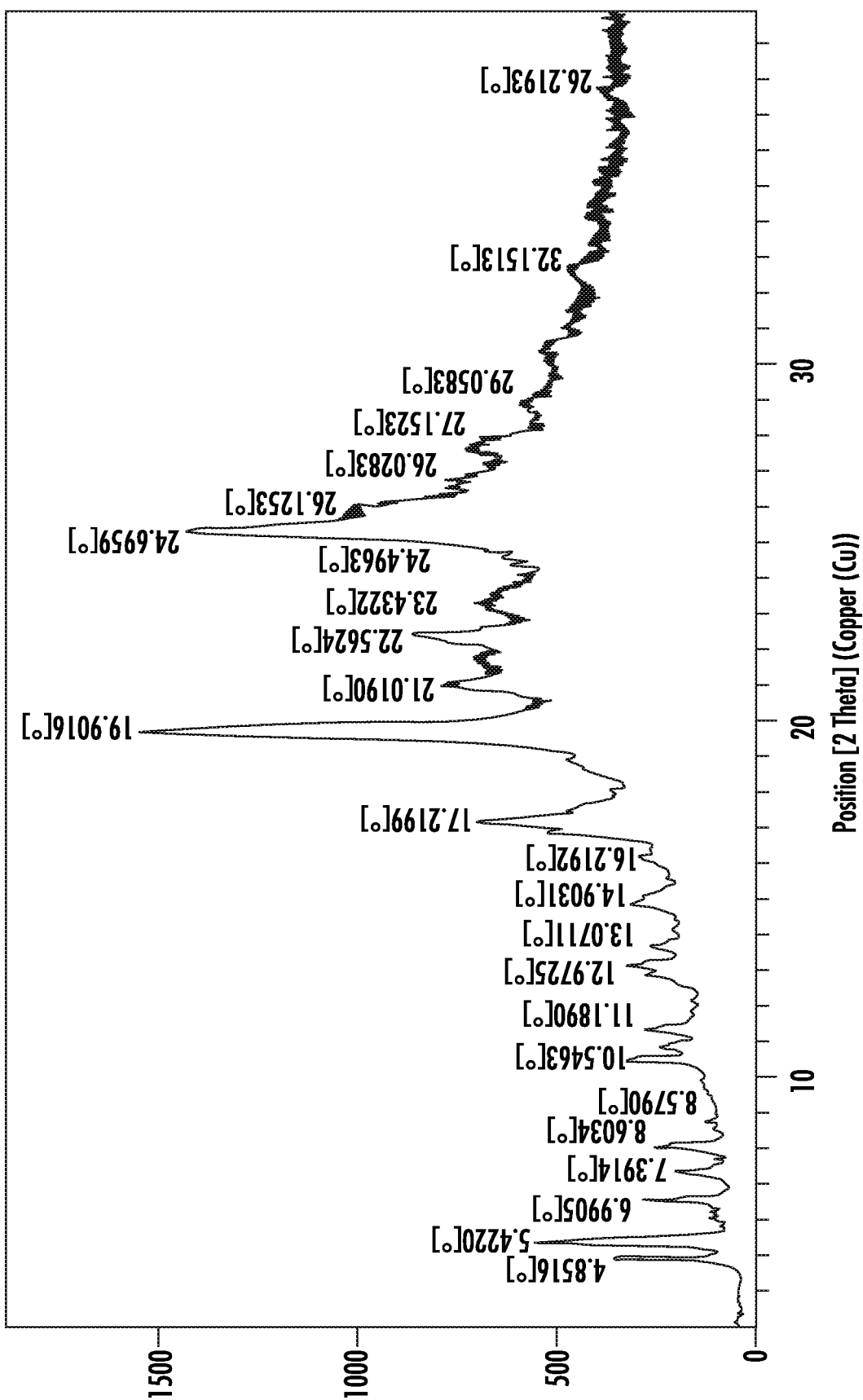
FIG. 15: represents an X-ray powder diffractogram of the crystalline form M of Afatinib dimaleate of the present invention

Crystalline form M of Afatinib dimaleate is characterized by at least one of:

a) an X-ray powder diffractogram having peaks at 5.0, 5.4, 17.3, 19.9 and 25.5±0.2 degrees two-theta;

b) an X-ray powder diffractogram substantially the same as depicted in FIG. 15
c) endothermic peaks at 112 and 172±2° C. as measured by differential scanning calorimetry (DSC); and
d) a weight loss of about 2.1±1% as measured by thermogravimetric analysis (TGA).

Crystalline form M of Afatinib dimaleate can be further characterized by its X-ray powder diffractogram having peaks at 5.0, 5.4, 6.6, 7.4, 8.1, 8.6, 10.5, 11.4, 12.9, 13.2, 13.7, 14.9, 16.2, 16.9, 17.3, 19.9, 21.0, 22.5, 23.4, 24.5, 25.5, 26.1, 26.9, 28.0, 29.1, 32.8 and 37.7±0.2 degrees two-theta.

Figure 16:
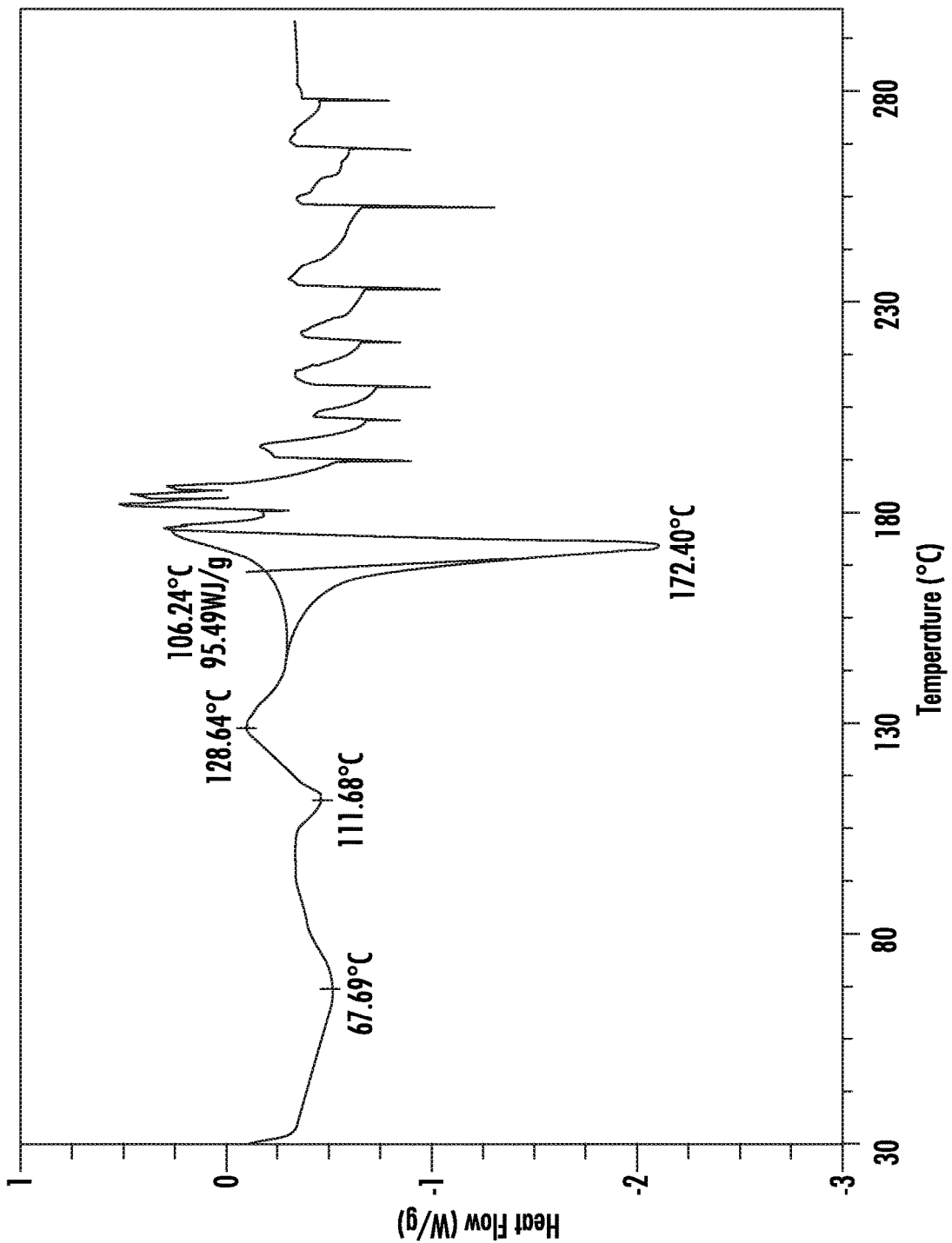
FIG. 16: represents a Differential Scanning calorimetry (DSC) thermogram of the crystalline form M of Afatinib dimaleate of the present invention

Crystalline form M of Afatinib dimaleate is further characterized by its DSC thermogram substantially the same as depicted in FIG. 16.

In an eighteenth aspect, the present invention relates to a process for the preparation of crystalline form M of Afatinib dimaleate, comprising,
a) dissolving Afatinib in acetonitrile;
b) adding solution of maleic acid in dimethyl sulfoxide and acetonitrile;
c) treating with ethyl acetate; and
d) isolating crystalline form M of Afatinib dimaleate.

Maleic acid in step b may be added as solution of maleic acid in acetonitrile and dimethyl sulfoxide.

The solution of Afatinib and maleic acid in acetonitrile and dimethyl sulfoxide may be obtained at ambient temperature to reflux, preferably at ambient temperature.

Crystalline form M of Afatinib dimaleate may be isolated by any one of the method selected from extraction, precipitation, cooling, filtration, centrifugation or mixture thereof. Preferably crystalline form M of Afatinib dimaleate is isolated by using vacuum filtration.

Crystalline form M of Afatinib dimaleate is optionally washed with ethyl acetate to reduce the organic volatile impurities content. After removal of the solvent the material is dried.

In a nineteenth aspect, the present invention relates to crystalline form E of Afatinib free base.

Figure 17:
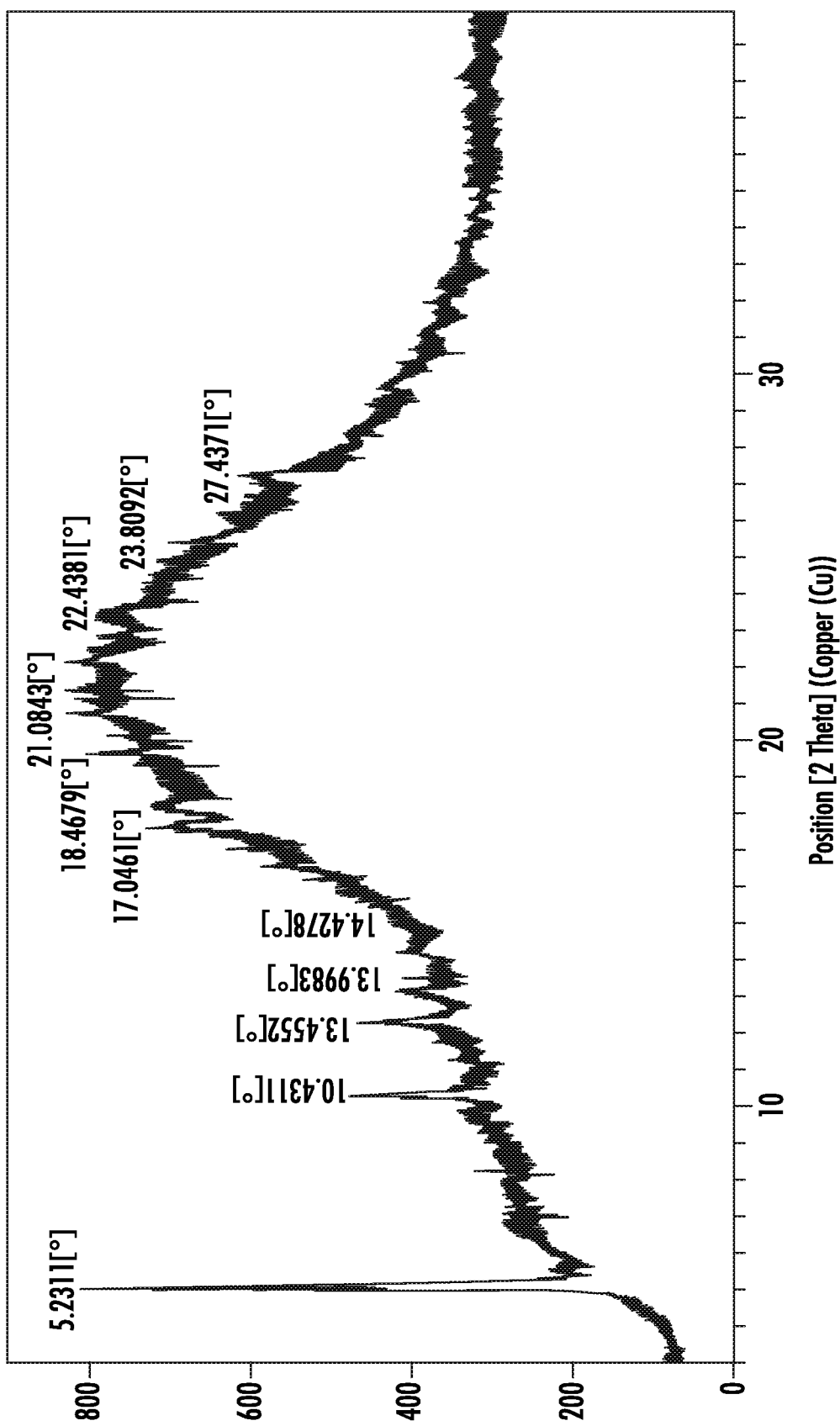
FIG. 17: represents an X-ray powder diffractogram of the crystalline form E of Afatinib free base of the present invention

Crystalline form E of Afatinib free base is characterized by at least one of:
a) an X-ray powder diffractogram having peaks at 5.2, 10.4, 12.4, 14.4±0.2 degrees two-theta;
b) an X-ray powder diffractogram substantially the same as depicted in FIG. 17,
c) an endothermic peak at 91±2° C. as measured by differential scanning calorimetry (DSC); and
d) a weight loss of about 2.3±1% as measured by thermogravimetric analysis (TGA).

Crystalline form E of Afatinib free base can be further characterized by its X-ray powder diffractogram having peaks at 5.2, 10.4, 12.4, 13.2, 14.4, 17.8, 18.5, 21.0, 22.5, 23.6 and 27.4±0.2 degrees two-theta.

Figure 18:
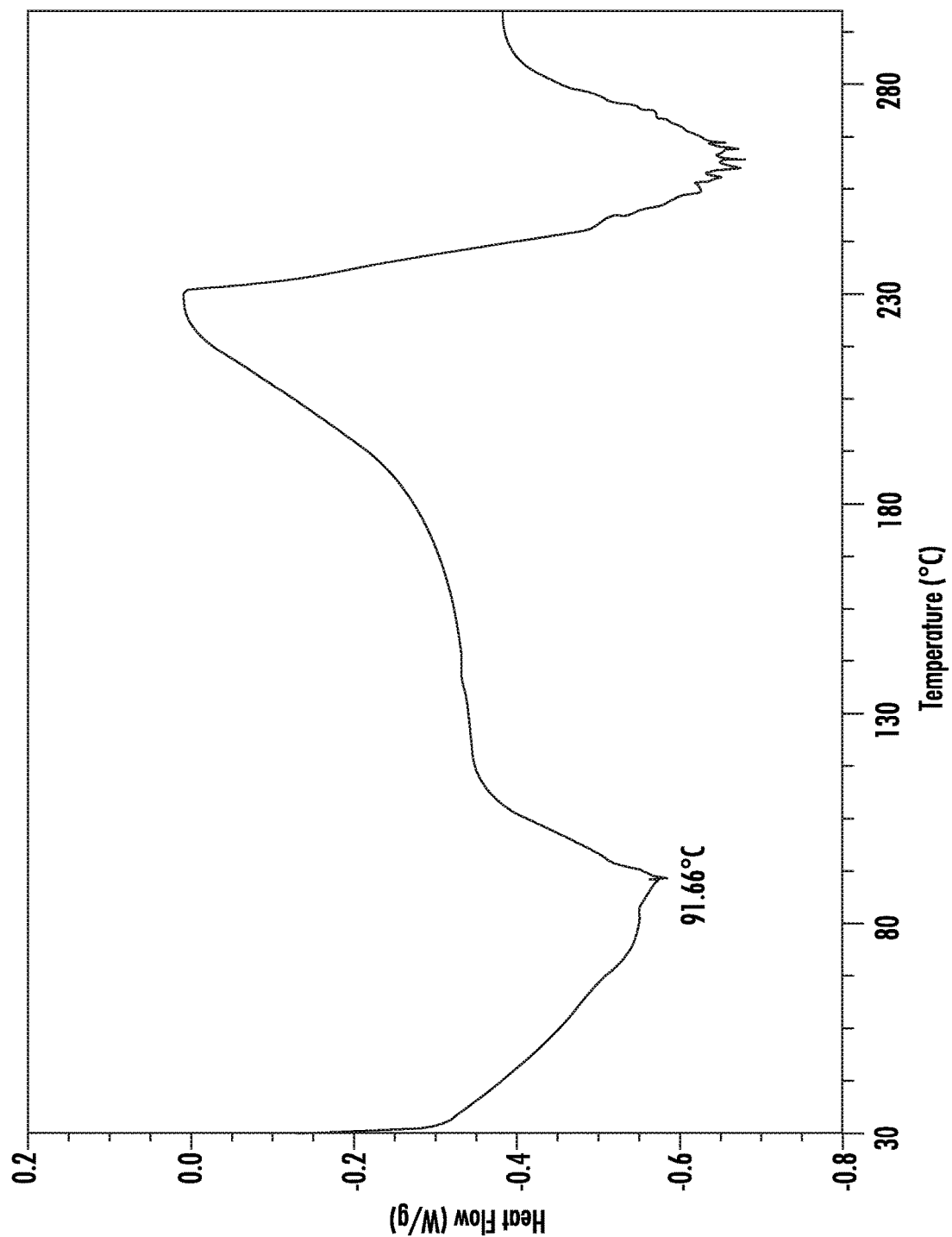
FIG. 18: represents a Differential Scanning calorimetry (DSC) thermogram of the crystalline form E of Afatinib free base of the present invention

Crystalline form E of Afatinib free base of the present invention is further characterized by its DSC thermogram substantially the same as depicted in FIG. 18.

In a twentieth aspect, the present invention relates to a process for the preparation of crystalline form E of Afatinib free base, comprising:
a) dissolving Afatinib in acetone;
b) adding methyl tertiary butyl ether; and
c) isolating crystalline form E of Afatinib free base.

The solution of Afatinib in acetone may be obtained at ambient temperature to reflux, preferably at ambient temperature.

It is preferred to cool the reaction mass after step b) from ambient temperature to −30° C., more preferably from −5° C. to −20° C.

Crystalline form E of Afatinib free base is optionally washed with methyl tertiarybutyl ether to reduce the content of organic volatile impurities. After removal of the solvent the material is dried.

Crystalline form E of Afatinib free base may be isolated by any one of the method such as extraction, precipitation, cooling, filtration, centrifugation or mixture thereof.

Preferably crystalline form E of Afatinib free base is isolated by using vacuum filtration.

In a twenty-first aspect, the present invention relates to crystalline form F of Afatinib free base.

Figure 19:
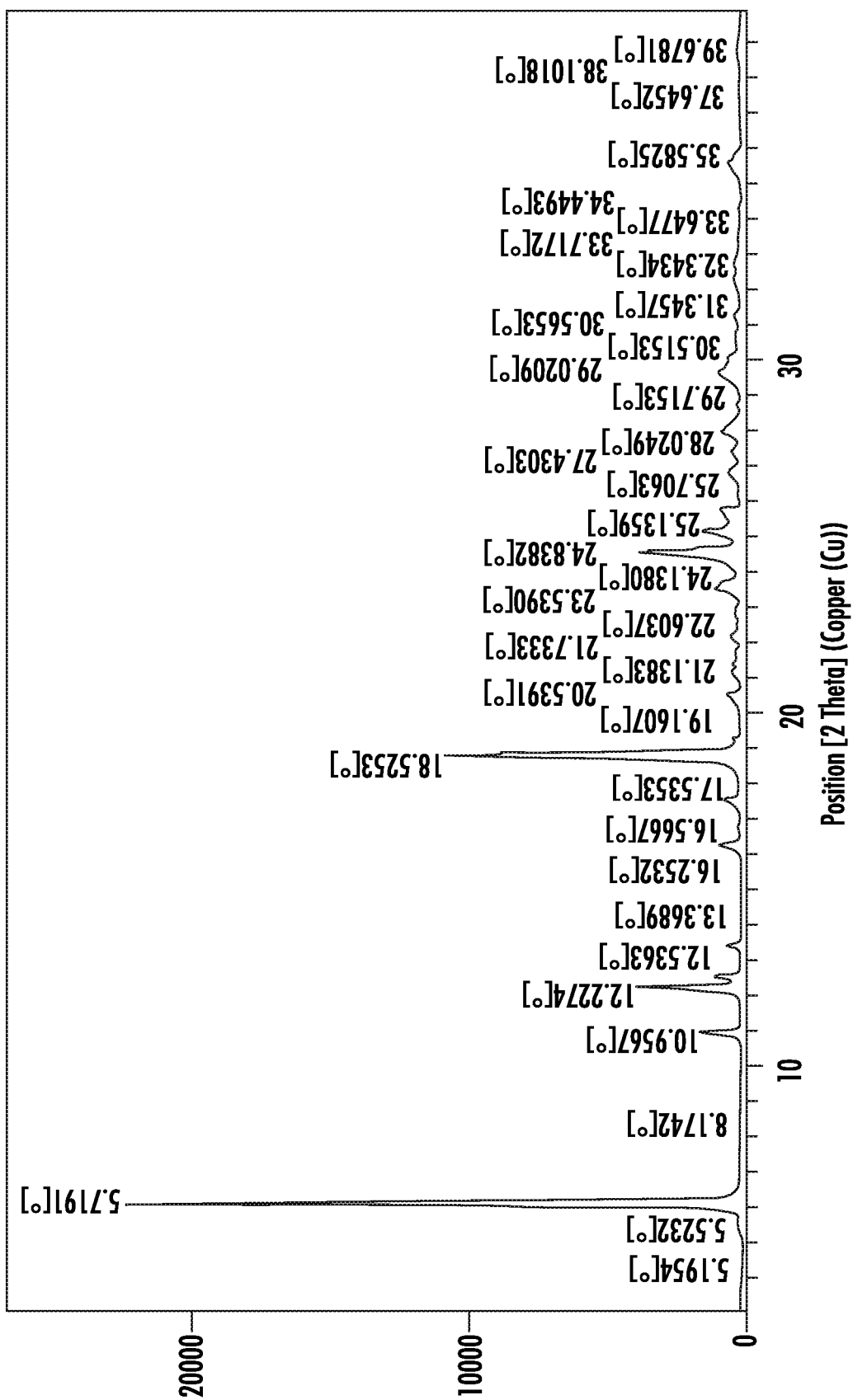
FIG. 19: represents an X-ray powder diffractogram of the crystalline form F of Afatinib free base of the present invention

Crystalline form F of Afatinib free base is characterized by at least one of:
a) an X-ray powder diffractogram having peaks at 6.1, 12.2, 13.4, 16.3, 18.8, 20.5 and 24.6±0.2 degrees two-theta;
b) an X-ray powder diffractogram substantially the same as depicted in FIG. 19;
c) an endothermic peak at 102±2° C. as measured by differential scanning calorimetry (DSC); and
d) by a weight loss of about 3.6±1% as measured by thermogravimetric analysis (TGA).

Crystalline form F of Afatinib free base of the present invention can be further characterized by its X-ray powder diffractogram having peaks at 5.2, 5.5, 6.1, 8.2, 10.9, 12.2, 12.5, 13.4, 16.3, 16.7, 17.5, 18.8, 19.2, 20.5, 21.1, 21.4, 21.7, 22.1, 22.5, 22.9, 23.6, 24.1, 24.6, 25.2, 25.7, 26.8, 26.9, 27.4, 28.0, 28.7, 29.7, 30.0, 30.5, 31.3, 32.3, 32.7, 33.6, 34.4, 35.6, 37.6, 38.1 and 38.6±0.2 degrees two-theta.

Figure 20:
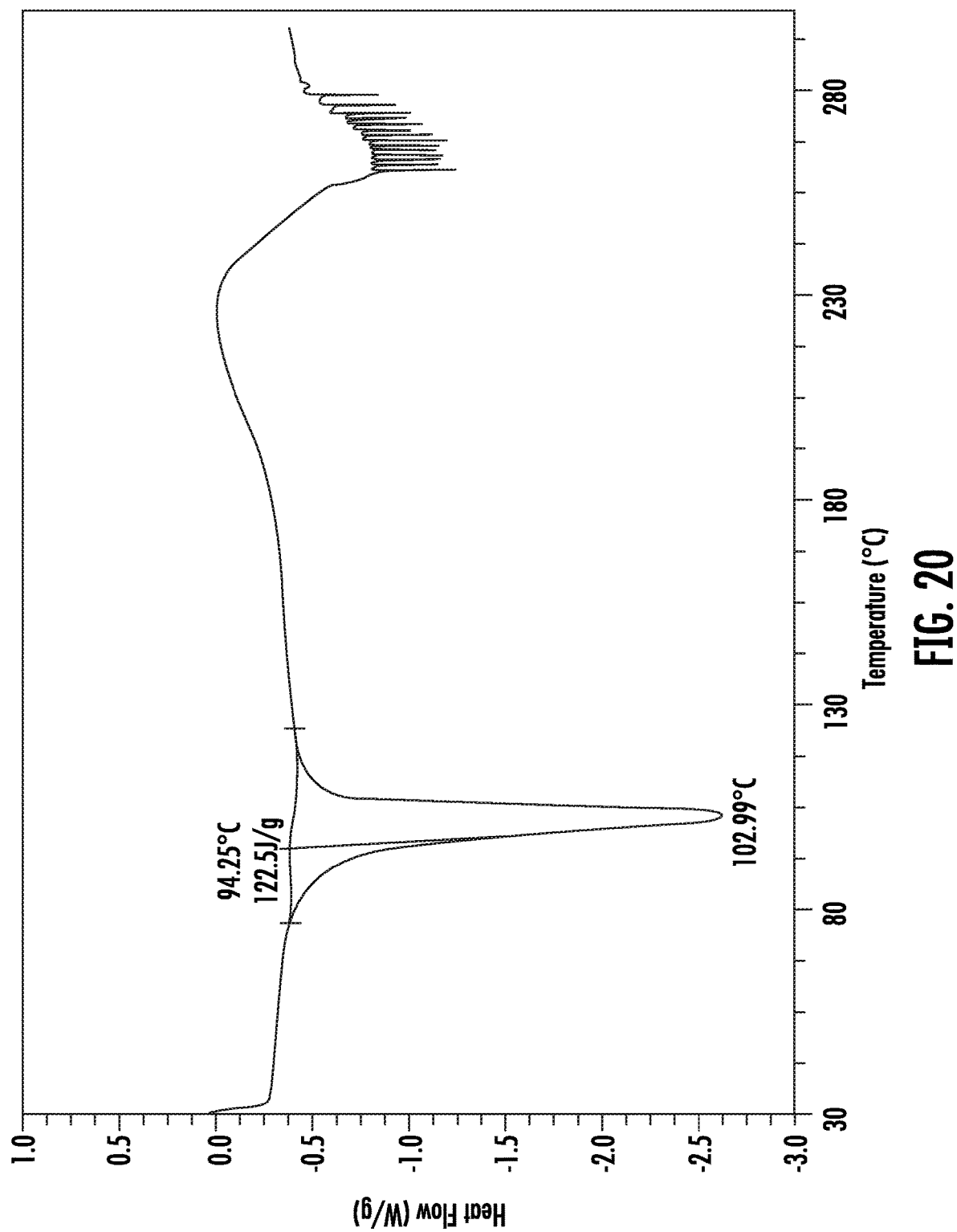
FIG. 20: represents a Differential Scanning calorimetry (DSC) thermogram of the crystalline form F of Afatinib free base of the present invention
Figure 21:
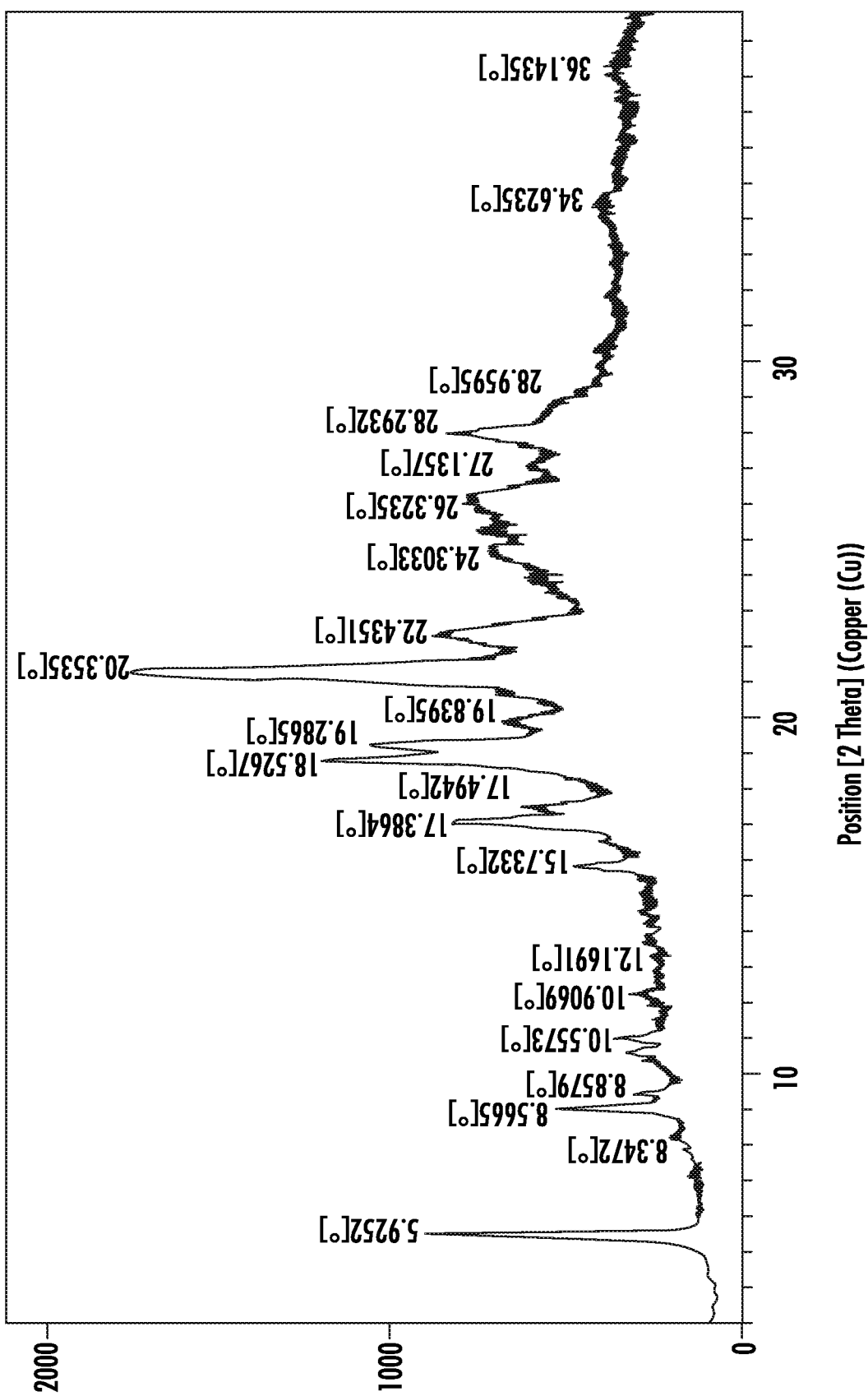
FIG. 21: represents an X-ray powder diffractogram of the crystalline form C of Afatinib dimaleate of the present invention
Figure 22:
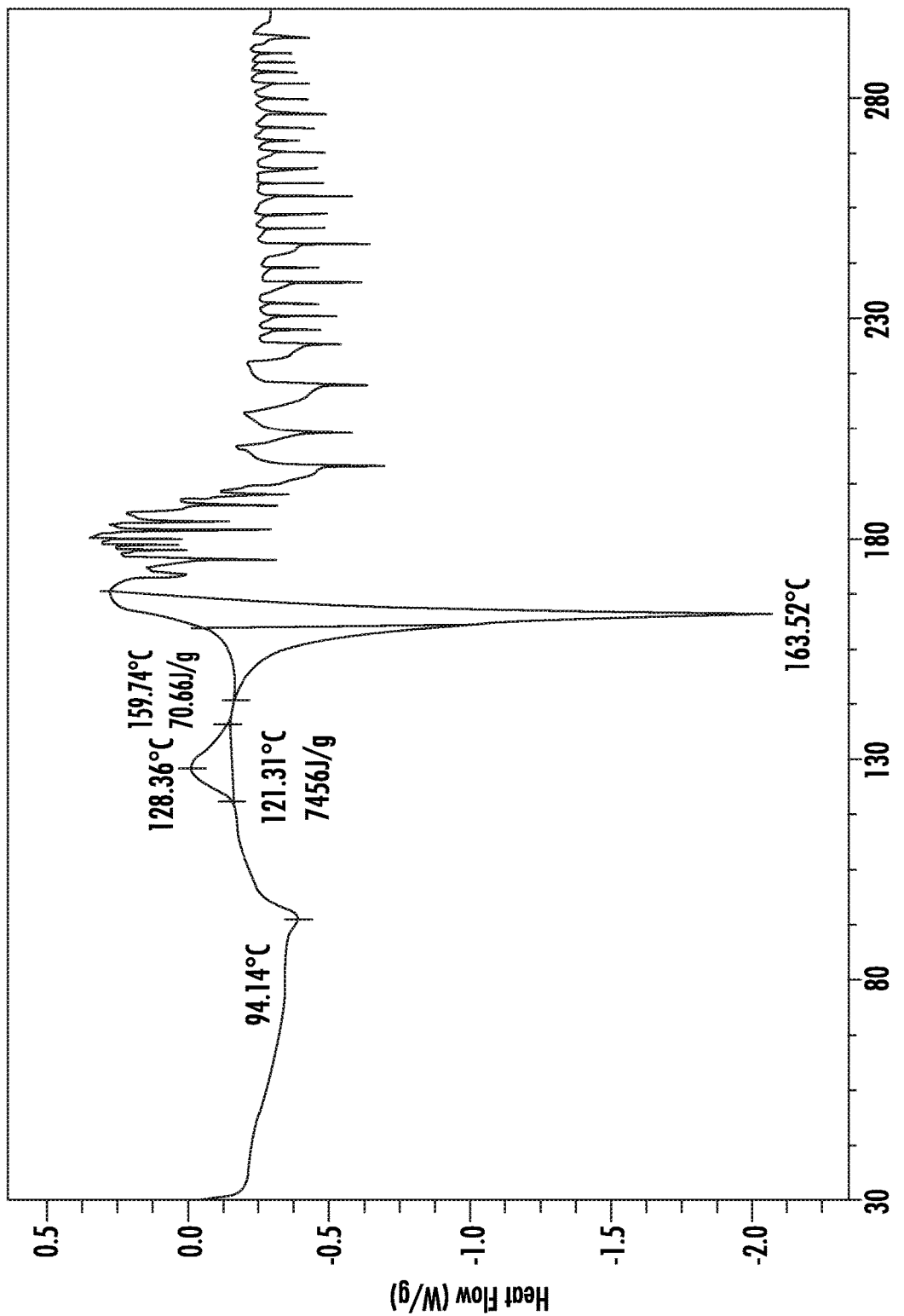
FIG. 22: represents a Differential Scanning calorimetry (DSC) thermogram of the crystalline form C of Afatinib dimaleate of the present invention

Crystalline form F of Afatinib free base of the present invention is further characterized by its Differential Scanning calorimetry (DSC) thermogram substantially the same as depicted in FIG. 20.

In a twenty-second aspect, the present invention relates to a process for the preparation of crystalline form F of Afatinib free base, comprising:
a) dissolving Afatinib in dichloromethane;
b) adding methyl tertiary butyl ether; and
c) isolating crystalline form F of Afatinib free base.

The solution of Afatinib in dichloromethane may be obtained at ambient temperature to reflux, preferably at ambient temperature.

It is preferred to cool the reaction mass after step b) from ambient temperature to −10° C., more preferably from 10° C. to −5° C.

Crystalline form F of Afatinib free base may be isolated by any one of the method selected from extraction, precipitation, cooling, filtration, centrifugation or mixture thereof. Preferably crystalline form F of Afatinib free base is isolated by using vacuum filtration.

The obtained crystalline form F of Afatinib free base is optionally washed with methyl tertiarybutyl ether to reduce the organic volatile impurities content. After removal of the solvent the material is dried.

In a twenty-third aspect, the present invention relates to a process for the preparation of crystalline form C of Afatinib dimaleate, comprising:
a) dissolving Afatinib in acetone:
b) adding maleic acid;
c) isolating crystalline form C of Afatinib dimaleate.

Maleic acid in step b may be added as a solution of maleic acid in acetone.

The solution of Afatinib and maleic acid in acetone may be obtained at ambient temperature to reflux, preferably at ambient temperature.

Crystalline form C of Afatinib dimaleate may be isolated by any one of the method extraction, precipitation, cooling, filtration, centrifugation or mixture thereof.

Preferably crystalline form C of Afatinib dimaleate is isolated by using vacuum filtration.

Crystalline form C of Afatinib dimaleate is optionally washed with acetone to reduce the content of organic volatile impurities. After removal of the solvent the material is dried.

In a twenty-fourth aspect, the present invention relates to a process for the preparation of crystalline form C of Afatinib dimaleate, comprising:
 c) treating crystalline form H of Afatinib dimaleate with acetone; and
 d) isolating crystalline form C of Afatinib dimaleate.

Crystalline form C of Afatinib dimaleate may be isolated by any one of the methods selected from extraction, precipitation, cooling, filtration, centrifugation or mixture thereof. Preferably, crystalline form C of Afatinib dimaleate is isolated by vacuum filtration.

Crystalline form C of Afatinib dimaleate is optionally washed with acetone to reduce the organic volatile impurities content. After removal of the solvent the material is dried.

In a twenty-fifth aspect, the present invention relates to a pharmaceutical composition comprising any of the above described crystalline forms of Afatinib dimaleate, designated as "form F" to "form M", or mixtures thereof and at least one pharmaceutically acceptable excipient.

In a twenty-sixth aspect, the present invention relates to the use of any one of the above described crystalline forms of Afatinib dimaleate, designated as "form F" to "form M" for the treatment of cancer, particularly for the treatment of solid tumors, including non-small cell lung cancer (NSCLC), breast, head and neck cancer, and a variety of other cancers.

Particularly a person suffering from a cancer may be mediated by epidermal growth factor receptor (EGFR) and human epidermal receptor 2 (HER2) tyrosine kinases, e.g., solid tumors including but not limited to NSCLC, breast, head and neck cancer, and a variety of other cancers mediated by EGFR or HER2 tyrosine kinases.

The methods for the preparation of the crystalline forms of Afatinib dimaleates and Afatinib free base of the present invention may be illustrated by way of the following examples, which is no way should be construed as limiting the scope of the invention.

EXAMPLES

Instruments
XRD
 X-ray diffraction data is obtained using a Bruker AXS D8 advance Powder X-ray Diffractometer, CuK☐ radiation, wavelength 1.54 Å.
DSC
 DSC measurement is performed using DSC (DSC Q2000, TA Instruments USA), equipped with RCS90 cooling accessory, weight of sample 2.6 mg, temperature range 30°-300° C., 10° C./min.
TGA:
 TGA measurement is performed using a TGA Q500 V20, temperature range 25°-300° C., 10° C./min.

Example 1: Preparation of Afatinib

A mixture of (E)-4-(dimethylamino) but-2-enoic acid hydrochloride (44.1 g) and dimethyl acetamide (350 ml) was cooled at −15 to −20° C. To this solution 28.6 g of thionyl chloride was added dropwise and stirred at −15 to −20° C. for 3-4 h (designated as solution-1). In a separate container $N^4$-(3-chloro-4-fluorophenyl)-7-[(3S)-tetrahydrofuran-3-yloxy]quinazoline-4,6-diamine (50 g) was dissolved in 150 ml dimethylacetamide and added to the solution-1 at −20 to −25° C. The reaction mixture was stirred for 1-2 h. To this reaction mass charged water (100 ml) followed by stirring for 10 min(designated as solution-2). A solution of sodium carbonate prepared separately by dissolving 125 g potassium carbonate in 1900 ml of purified water (designated as solution-3). The solution-2 was added into the solution-3 and solid obtained stirred for 2-3 hr. The solid was filtered and suspended in water and pH adjusted to 2-5 using hydrochloric acid solution. Ethyl acetate (500 ml) added and reaction mass stirred for 1-1.5 h. Ethyl acetate layer separated and discarded. The aqueous layer was neutralized with potassium carbonate and pH was maintained at around 8-9. The solid obtained stirred for further 2 h and filtered followed by drying to get 48 g of the Afatinib free base.

Example 2: Preparation of Crystalline Form F of Afatinib Dimaleate

A mixture of ethyl acetate (60 ml) and Afatinib (3.0 g) was stirred at 20-30° C. to get a clear solution. A solution of maleic acid [prepared by dissolving 1.54 g of maleic acid in 45 ml of ethyl acetate] was added to the above solution in 10-15 min at 20-30° C. The reaction mass was stirred for 2 h at 20-30° C. The solid thus formed was filtered, washed with ethyl acetate (15 ml) and dried at 40° C. for 10 h. 4 g of crystalline form F of Afatinib dimaleate was obtained.
 Water Content: 4.54% (w/w)

Example-3: Preparation of Crystalline Form G of Afatinib Dimaleate

A solution of Afatinib (3.0 g) in dimethyl formamide (15 ml) was stirred at 20-30° C. Another solution was prepared by dissolving maleic acid (1.50 g) in dimethyl formamide (6.0 ml) and added to the previous solution. The reaction mixture was stirred for 15 min and then cooled to 0-10° C. Methyl tertiary butyl ether (90 ml) was added to resulting solution in 15 min and stirred for 2 h at 0-10° C. The resulting solid was filtered, washed with methyl tertiary butyl ether (30 ml) and suck dried for 10 min under vacuum at 40° C. for 10 h. 4 g of crystalline form G of Afatinib dimaleate was obtained.
 Water Content: 0.46% (w/w)

Example-4: Preparation of Crystalline Form H of Afatinib Dimaleate

A solution of Afatinib (3.0 g) in acetonitrile (60 ml) was stirred at 20-30° C. for 10 min. A separately prepared solution of maleic Acid (prepared by dissolving maleic acid (1.50 g) in 45 ml of acetonitrile) was added and the reaction mass was stirred overnight. The solid thus obtained was filtered, washed with acetonitrile (30 ml), suck dried for 10 min and then dried under vacuum at 40° C. for 10 h. 3 g of crystalline form H of Afatinib dimaleate was obtained.
 Water Content: 1.22% (w/w)

Example-5: Preparation of Crystalline Form I of Afatinib Dimaleate

A solution of Afatinib (2.0 g) in dimethylformamide (4 ml) was stirred at 20-30° C. for 5 min. A separately prepared solution of maleic acid (prepared by dissolving 1.0 g of maleic acid in 2 ml of dimethylformamide) was added to above solution in 10 min. Thereafter, dichloromethane (60 ml) was added in 20 min period and mixture was stirred for 2 h. Product thus obtained was filtered and washed with dichloromethane (20 ml). After suck drying for 30 min, the solid was again suspended in dichloromethane (40 ml) and stirred for 1 h. The product was filtered, washed with dichloromethane (20 ml) and suck dried for 30 min. Resulting solid was further dried under vacuum at 50-60° C. for 12 h. 2.2 g of crystalline form I of Afatinib dimaleate was obtained.

Water Content: 2.8500

Example-6: Preparation of Crystalline Form J of Afatinib Dimaleate

A solution of Afatinib (5.0 g) in acetone (125 ml) was stirred at 20-30° C. for 10 min. methyl tertiary butyl ether (100 ml) was charged in 10 min. Maleic acid solution [Prepared by dissolving maleic acid (2.5 g) in acetone (25 ml)] was added in the reaction mass. The reaction mass was stirred for 2 h at 20-30° C. The solid thus formed was filtered and washed with methyl tertiary butyl ether (50 ml). The product was suck dried for 15 min. and under vacuum at 40° C. for 12 h. 6.5 g of crystalline form J of Afatinib dimaleate was obtained.

Water Content: 1.46%

Example-7: Preparation of Crystalline Form K of Afatinib Dimaleate

A solution of Afatinib (5.0 g) in ethyl acetate (100 ml) was stirred at 20-30° C. for 10-15 min. Methyl tertiary butyl ether (100 ml) was added and the solution was stirred for 15 min at 25-30° C. A solution of maleic acid [prepared by dissolving maleic acid (2.5 g) in ethyl acetate (75 ml)] was added in the reaction mixture and stirred for 24 h at 25-30° C. The solid thus formed was filtered and washed with methyl tertiary butyl ether (40 ml) followed by suck drying for 15 min. The product was finally dried under vacuum at 40° C. for 24 h. 6.3 g of crystalline form K of Afatinib dimaleate was obtained.

Water Content: 2.27%

Example-8: Preparation of Crystalline Form L of Afatinib Dimaleate

A solution of Afatinib (9.0 gm) in acetonitrile (180 ml) was stirred at 20-30° C. for 10 min. A solution of maleic Acid [prepared by dissolving maleic acid (4.5 g) in acetonitrile (180 ml)] was added to the solution slowly at 20-30° C. in 20 min. The reaction mass was stirred for 2 h followed by filtration. The solid thus obtained was washed with acetonitrile (18.0 ml) and suck dried for 15 min. The solid was further dried under vacuum for 6.0 hr at 25° C. The dried material (7.0 g) was charged in a flask followed by addition of ethyl acetate (70 ml) and stirred for 2 h at 20-30° C. The solid was filtered and washed with ethyl acetate (20 ml) and suck dried for 15 min. The product finally dried in oven under vacuum at 45° C. for 15-16 h. 8.4 g of crystalline form L of Afatinib dimaleate was obtained Water Content: 1.61%

Example-9: Preparation of Crystalline Form M of Afatinib Dimaleate

A solution of Afatinib (15.0 g) in acetonitrile (300 ml) was stirred at room temperature for 30 min. The clear solution was filtered through 5 micron filter paper. The filtrate was charged in the flask and ⅔ of maleic acid solution [prepared by dissolving maleic acid (9.1 g) in dimethylsulfoxide (10 ml) and acetonitrile (10 ml] was added drop wise. The reaction mass was stirred for 15-20 min followed by addition of rest of the maleic acid solution. After complete addition the reaction mass was stirred for 1-2 h at 20-35° C. The solid thus formed was filtered and washed with acetonitrile (15 ml) and suck dried for 10-15 min. The product thus obtained was charged in the reactor and acetonitrilec (150 ml) was added. The reaction mas was stirred for 15 min and then filtered under nitrogen. The product was washed with acetonitrile (15 ml 2). The product was suck dried for 1-2 h and then dried under vacuum (NLT 700 mmHg) for 5-6 h. The resulting product was charged in a flask and ethyl acetate (600 ml) was added and reaction mass was stirred for 90 min. The solid thus formed was filtered, washed with ethyl acetate (150 ml) and suck dried for 20-30 min. and finally under vacuum (NLT 700 mmHg) at 45° C. for 20-22 h. 18.8 g of crystalline form M of Afatinib dimaleate was obtained Water Content: 2.54%

Example-10: Preparation of Crystalline Form E Afatinib Free Base

A solution of Afatinib (55.0 g) in acetone (165 ml) was stirred for 20-30 min at room temperature. Methyl tertiary butyl ether (165 ml) was added and the reaction mass was cooled to −10 to −15° C. The reaction mass was stirred for 1-2 h at −10 to −15° C. The solid thus obtained was filtered and washed with chilled methyl tertiary butyl ether (55 ml). The solid was suck dried for 1-2 h followed by drying under reduced pressure NLT (700 mmHg) for 10-12 h. 48 g of crystalline form E of Afatinib free base was obtained.

Water Content: 2.2600

Example-11: Preparation of Crystalline Form F Afatinib Free Base

To a solution of Afatinib (50.0 g) in dichloromethane (350 ml) methyl tertiary butyl ether (350 ml) was added slowly over a period of 30 min. The reaction mass was stirred for 1 h at 20-30° C. followed by cooling at 0-5° C. The reaction mass was continue to stirred for 1 h at 0-5° C. and solid thus formed was filtered and washed with chilled methyl tertiarybutyl ether 100 ml). The solid was suck dried for 1 h at room temperature and further at 50° C. under reduced pressure NLT (700 mmHg) for 12 h. 48 g form F of Afatinib free base was obtained.

Water Content: 3.71° %

Example-12: Preparation of Crystalline Form C Afatinib Dimaleate

In a solution of Afatinib (3.0 g) in acetone (90 ml), maleic acid solution [prepared by dissolving maleic acid (1.54 g) in acetone (15 ml)] was added in 6 min at 20-30° C. The reaction mass was stirred for 2 h at 20-30° C. The solid product thus obtained was filtered and washed with acetone (15 ml). The filtered product was suck dried for 15 min and then under vacuum at 40° C. for 10 h.

Water Content: 1.52%

Example-13: Preparation of Crystalline Form C of Afatinib Dimaleate

In a solution of Afatinib (10.0 gm) in acetonitrile (200 ml), maleic acid solution [prepared by dissolving maleic acid (5.0 g) in acetonitrile (100 ml)] was added at 20-30° C. The reaction mass was stirred for 2 h and solid was filtered. The wet cake thus obtained was washed with acetonitrile (20 ml) and suck dried for 15 min. The suck dried material was further dried under reduced pressure (NLT 700 mmHg) for 6 h at 25° C. Vacuum dried Afatinib dimaleate (2.0 g) was charged in a flask and acetone was (20 ml) added. The reaction mass was stirred at 20-25° C. for 2 h and then filtered. The product thus obtained was washed with acetone (20 ml) and suck dried for 15 min. Finally the material was dried at 45° C. under reduced pressure (NLT 700 mm Hg) for 15-16 h.

Water Content: 2.06%

The invention claimed is:

1. A crystalline form L of Afatinib dimaleate characterized by:
    a) an X-ray powder diffractogram having peaks at 5.2, 10.3, 11.1, 15.5, 18.1±0.2 degrees two-theta; and
    b) endothermic peaks at 125 and 171±2° C. as measured by differential scanning calorimetry (DSC).

2. A process for preparing the crystalline form L of Afatinib dimaleate according to claim 1 comprising:
    a) treating crystalline form H of Afatinib dimaleate with ethyl acetate; and
    b) isolating the crystalline form L of Afatinib dimaleate, wherein the crystalline form H of Afatinib dimaleate is characterized by:
        an X-ray powder diffractogram having peaks at 5.4, 6.5, 10.2, 12.7, 17.7, 21.7, and 25.3±0.2 degrees two-theta.

3. A process for preparing crystalline form L of Afatinib dimaleate, comprising:
    a) reacting a compound of Formula II

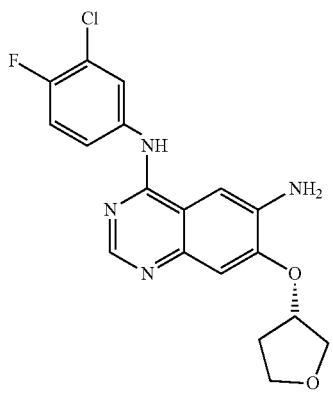

Formula II with a compound of Formula III or a salt thereof

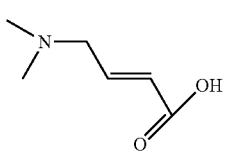

Formula III in the presence of a solvent and a dehydrating reagent, at a temperature between −40° C. and 0° C. to obtain Afatinib of Formula I

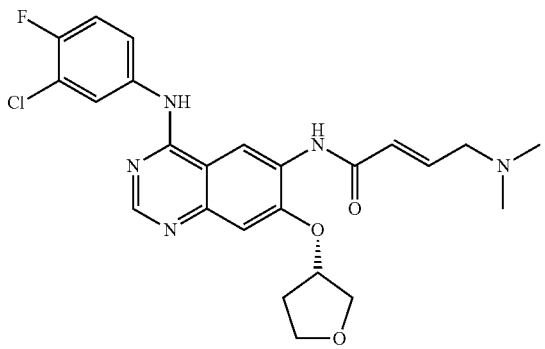

Formula I b) dissolving the Afatinib of Formula I in acetonitrile;
   c) adding maleic acid;
   d) isolating crystalline form H of Afatinib dimaleate;
   e) treating crystalline the form H of Afatinib dimaleate with ethyl acetate; and
   f) isolating the crystalline form L of Afatinib dimaleate.

4. The process according to claim 3, wherein the temperature is kept between −25° C. and −10° C. during step a).

5. The process according to claim 3, wherein the dehydrating agent is thionyl chloride.

6. The process according to claim 3, wherein the solvent is selected from hydrocarbons, esters, ketones, halogenated hydrocarbons, ethers, nitriles, alcohols, amides, sulfoxides and mixtures thereof.

7. The process according to claim 3, wherein the solvent is an amide.

8. The process according to claim 7, wherein the amide is dimethylacetamide.

9. A crystalline form L of Afatinib dimaleate, characterized by a) an X-ray powder diffractogram substantially the same as depicted in FIG. 13; and b) endothermic peaks at 125 and 171±2° C. as measured by differential scanning calorimetry (DSC).

10. The crystalline form L of Afatinib dimaleate according to claim 1, characterized by a weight loss of about 2.0±1% as measured by thermogravimetric analysis (TGA).

11. The crystalline form L of Afatinib dimaleate according to claim 9, characterized by a weight loss of about 2.0±1% as measured by thermogravimetric analysis (TGA).

12. The process of claim 2, wherein the crystalline form H of Afatinib dimaleate is characterized by an endothermic peak at 118±2° C. as measured by differential scanning calorimetry (DSC).

13. The process of claim 2, wherein the crystalline form H of Afatinib dimaleate is characterized by a weight loss of about 0.6±1% as measured by thermogravimetric analysis (TGA).

14. The process of claim 12, wherein the crystalline form H of Afatinib dimaleate is characterized by a weight loss of about 0.6±1% as measured by thermogravimetric analysis (TGA).

15. The process for preparing the crystalline form L of Afatinib dimaleate according to claim 2, wherein the crystalline form H of Afatinib dimaleate is characterized by an X-ray powder diffractogram substantially the same as depicted in FIG. 5.

16. A process for preparing the crystalline form L of Afatinib dimaleate according to claim 1 comprising:
    a) treating crystalline form H of Afatinib dimaleate with ethyl acetate; and b) isolating the crystalline form L of Afatinib dimaleate, wherein the crystalline form H of Afatinib dimaleate is characterized by an X-ray powder diffractogram substantially the same as depicted in FIG. 5.

17. A process for preparing the crystalline form L of Afatinib dimaleate according to claim 9 comprising:
  a) treating crystalline form H of Afatinib dimaleate with ethyl acetate; and
  b) isolating the crystalline form L of Afatinib dimaleate, wherein the crystalline form H of Afatinib dimaleate is characterized by an X-ray powder diffractogram having peaks at 5.4, 6.5, 10.2, 12.7, 17.7, 21.7, and 25.3±0.2 degrees two-theta.

18. A process for preparing the crystalline form L of Afatinib dimaleate according to claim 9 comprising:
  a) treating crystalline form H of Afatinib dimaleate with ethyl acetate; and
  b) isolating the crystalline form L of Afatinib dimaleate, wherein the crystalline form H of Afatinib dimaleate is characterized by an X-ray powder diffractogram substantially the same as depicted in FIG. 5.

19. The process of claim 2, wherein the crystalline form H of Afatinib dimaleate is characterized by an X-ray powder diffractogram substantially the same as depicted in FIG. 5 and an endothermic peak at 118±2° C. as measured by differential scanning calorimetry (DSC).

20. The process of claim 17, wherein the crystalline form H of Afatinib dimaleate is characterized by a weight loss of about 0.6±1% as measured by thermogravimetric analysis (TGA).

21. The process of claim 19, wherein the crystalline form H of Afatinib dimaleate is characterized by a weight loss of about 0.6±1% as measured by thermogravimetric analysis (TGA).

* * * * *